US008474460B2

(12) United States Patent
Barrett et al.

(10) Patent No.: US 8,474,460 B2
(45) Date of Patent: Jul. 2, 2013

(54) IMPLANTED BRONCHIAL ISOLATION DEVICES AND METHODS

(75) Inventors: Michael Barrett, Campbell, CA (US); Michael Hendricksen, Redwood City, CA (US); Alan R. Rapacki, Redwood City, CA (US); Ronald R. Hundertmark, San Mateo, CA (US); Jeffrey J. Dolin, Belmont, CA (US); Robert M. George, San Jose, CA (US); Antony J. Fields, San Francisco, CA (US); Mark E. Deem, Mountain View, CA (US); Hanson S. Gifford, III, Woodside, CA (US); Ronald French, San Jose, CA (US); Douglas Sutton, Pacifica, CA (US)

(73) Assignee: Pulmonx Corporation, Redwood City, CA (US)

( * ) Notice: Subject to any disclaimer, the term of this patent is extended or adjusted under 35 U.S.C. 154(b) by 0 days.

(21) Appl. No.: 12/885,199

(22) Filed: Sep. 17, 2010

(65) Prior Publication Data

US 2011/0226238 A1    Sep. 22, 2011

Related U.S. Application Data

(63) Continuation-in-part of application No. 11/075,633, filed on Mar. 8, 2005, now abandoned, and a continuation-in-part of application No. 12/264,849, filed on Nov. 4, 2008, now Pat. No. 8,357,139, which is a continuation of application No. 10/630,473, filed on Jul. 29, 2003, now Pat. No. 7,165,548, which is a continuation of application No. 09/519,735, filed on Mar. 4, 2000, now Pat. No. 6,679,264.

(60) Provisional application No. 60/551,476, filed on Mar. 8, 2004.

(51) Int. Cl.
*A62B 9/02*    (2006.01)

(52) U.S. Cl.
USPC .................................................. 128/207.16

(58) Field of Classification Search
USPC .......... 604/34, 99.03, 506, 31, 99.04, 167.04, 604/247, 249, 288.03; 623/9, 23.65; 600/529; 424/45, 423, 1.25; 128/200.23, 207.16, 207.15, 128/207.14, 200.24
See application file for complete search history.

(56) References Cited

U.S. PATENT DOCUMENTS

| 2,981,254 A | 4/1961 | Vanderbilt |
| 3,657,744 A | 4/1972 | Ersek |

(Continued)

FOREIGN PATENT DOCUMENTS

| DE | 9205797 U1 | 6/1992 |
| EP | 0621015 A1 | 10/1994 |

(Continued)

OTHER PUBLICATIONS

Al Jishi et al., "Selective Bronchial Occlusion for Treatment of Bullous Interstitial Emphysema and Bronchopleural Fistula." J. of Pediatric Surgery, 29:1545-1547, 1994.

(Continued)

*Primary Examiner* — Theodore Stigell
*Assistant Examiner* — Brooke Matney
(74) *Attorney, Agent, or Firm* — Wilson, Sonsini, Goodrich & Rosati

(57) ABSTRACT

Disclosed are methods and devices for regulating fluid flow to and from a region of a patient's lung, such as to achieve a desired fluid flow dynamic to a lung region during respiration and/or to induce collapse in one or more lung regions. Pursuant to an exemplary procedure, an identified region of the lung is targeted for treatment. The targeted lung region is then bronchially isolated to regulate airflow into and/or out of the targeted lung region through one or more bronchial passageways that feed air to the targeted lung region.

13 Claims, 17 Drawing Sheets

U.S. PATENT DOCUMENTS

| | | |
|---|---|---|
| 3,667,069 A | 6/1972 | Blackshear et al. |
| 3,788,327 A | 1/1974 | Donowitz et al. |
| 3,874,388 A | 4/1975 | King et al. |
| 4,014,318 A | 3/1977 | Dockum et al. |
| 4,086,665 A | 5/1978 | Poirier |
| 4,212,463 A | 7/1980 | Repinski et al. |
| 4,250,873 A | 2/1981 | Bonnet |
| 4,302,854 A | 12/1981 | Runge |
| 4,477,930 A | 10/1984 | Totten et al. |
| 4,710,192 A | 12/1987 | Liotta et al. |
| 4,732,152 A | 3/1988 | Wallsten et al. |
| 4,759,758 A | 7/1988 | Gabbay |
| 4,774,942 A | 10/1988 | Moellers |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,879,998 A | 11/1989 | Moellers |
| 4,934,999 A | 6/1990 | Bader |
| 4,968,294 A | 11/1990 | Salama |
| 4,990,151 A | 2/1991 | Wallsten |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,158,548 A | 10/1992 | Lau et al. |
| 5,161,524 A | 11/1992 | Evans |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,453,090 A | 9/1995 | Martinez et al. |
| 5,474,099 A | 12/1995 | Boehmer et al. |
| 5,486,154 A | 1/1996 | Kelleher |
| 5,499,995 A | 3/1996 | Teirstein |
| 5,500,014 A | 3/1996 | Quijano et al. |
| 5,522,881 A | 6/1996 | Lentz |
| 5,562,608 A | 10/1996 | Sekins et al. |
| 5,588,424 A | 12/1996 | Insler et al. |
| 5,645,519 A | 7/1997 | Lee et al. |
| 5,645,565 A | 7/1997 | Rudd et al. |
| 5,649,906 A | 7/1997 | Gory et al. |
| 5,660,175 A | 8/1997 | Dayal |
| 5,662,713 A | 9/1997 | Andersen et al. |
| 5,683,451 A | 11/1997 | Lenker et al. |
| 5,697,968 A | 12/1997 | Rogers et al. |
| 5,755,770 A | 5/1998 | Ravenscroft |
| 5,800,339 A | 9/1998 | Salama |
| 5,803,080 A | 9/1998 | Freitag |
| 5,824,037 A | 10/1998 | Fogarty et al. |
| 5,840,081 A | 11/1998 | Andersen et al. |
| 5,843,158 A | 12/1998 | Lenker et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,868,779 A | 2/1999 | Ruiz |
| 5,891,195 A | 4/1999 | Klostermeyre et al. |
| 5,910,144 A | 6/1999 | Hayashi |
| 5,944,738 A | 8/1999 | Amplatz et al. |
| 5,947,997 A | 9/1999 | Pavcnik et al. |
| 5,954,765 A | 9/1999 | Ruiz |
| 5,954,766 A | 9/1999 | Zadno-Azizi et al. |
| 5,957,949 A | 9/1999 | Leonhardt et al. |
| 5,976,174 A | 11/1999 | Ruiz |
| 5,980,455 A | 11/1999 | Daniel et al. |
| 5,984,965 A | 11/1999 | Knapp et al. |
| 5,989,288 A | 11/1999 | Pintauro et al. |
| 6,007,575 A | 12/1999 | Samuels |
| 6,009,614 A | 1/2000 | Morales |
| 6,020,380 A | 2/2000 | Killian |
| 6,022,312 A | 2/2000 | Chaussy et al. |
| 6,027,508 A | 2/2000 | Ren et al. |
| 6,027,525 A | 2/2000 | Suh et al. |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,162,245 A | 12/2000 | Jayaraman |
| 6,168,614 B1 | 1/2001 | Andersen et al. |
| 6,174,323 B1 | 1/2001 | Biggs et al. |
| 6,183,520 B1 | 2/2001 | Pintauro et al. |
| 6,190,381 B1 | 2/2001 | Olsen et al. |
| 6,200,333 B1 | 3/2001 | Laufer |
| 6,206,918 B1 | 3/2001 | Campbell et al. |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,247,471 B1 | 6/2001 | Bower et al. |
| 6,258,100 B1 | 7/2001 | Alferness et al. |
| 6,270,527 B1 | 8/2001 | Campbell et al. |
| 6,280,464 B1 | 8/2001 | Hayashi |
| 6,287,290 B1 | 9/2001 | Perkins et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,458,076 B1 | 10/2002 | Pruitt |
| 6,485,407 B2 | 11/2002 | Alferness et al. |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,527,761 B1 | 3/2003 | Soltesz et al. |
| 6,558,318 B1 | 5/2003 | Daniel et al. |
| 6,592,594 B2 | 7/2003 | Rimbaugh et al. |
| 6,632,243 B1 | 10/2003 | Zadno-Azizi et al. |
| 6,679,264 B1 | 1/2004 | Deem et al. |
| 6,694,979 B2 | 2/2004 | Deem et al. |
| 6,699,231 B1 | 3/2004 | Sterman et al. |
| 6,840,243 B2 | 1/2005 | Deem et al. |
| 6,878,141 B1 | 4/2005 | Perkins et al. |
| 6,901,927 B2 | 6/2005 | Deem et al. |
| 6,904,909 B2 | 6/2005 | Andreas et al. |
| 6,941,950 B2 | 9/2005 | Wilson et al. |
| 2001/0025132 A1 | 9/2001 | Alferness et al. |
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0026233 A1 | 2/2002 | Shaknovich |
| 2002/0062120 A1 | 5/2002 | Perkins et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0138135 A1 | 9/2002 | Duerig et al. |

| | | | |
|---|---|---|---|
| 2002/0173856 A1 | 11/2002 | Karason | |
| 2002/0177894 A1 | 11/2002 | Acosta et al. | |
| 2003/0018327 A1 | 1/2003 | Truckai et al. | |
| 2003/0018344 A1 | 1/2003 | Kaji et al. | |
| 2003/0050648 A1 | 3/2003 | Alferness et al. | |
| 2003/0070682 A1 | 4/2003 | Wilson et al. | |
| 2003/0070683 A1 | 4/2003 | Deem et al. | |
| 2003/0075169 A1 | 4/2003 | Deem et al. | |
| 2003/0075170 A1 | 4/2003 | Deem et al. | |
| 2003/0083671 A1 | 5/2003 | Rimbaugh et al. | |
| 2003/0127090 A1 | 7/2003 | Gifford et al. | |
| 2003/0164168 A1 | 9/2003 | Shaw et al. | |
| 2003/0192550 A1 | 10/2003 | Deem et al. | |
| 2003/0192551 A1 | 10/2003 | Deem et al. | |
| 2003/0199972 A1 | 10/2003 | Zadno-Azizi et al. | |
| 2003/0212452 A1 | 11/2003 | Zadno-Azizi et al. | |
| 2003/0228344 A1 | 12/2003 | Field et al. | |
| 2004/0016435 A1 | 1/2004 | Deem et al. | |
| 2004/0039250 A1 | 2/2004 | Tholfsen et al. | |
| 2004/0055606 A1 | 3/2004 | Hendricksen et al. | |
| 2004/0060563 A1 | 4/2004 | Rapacki et al. | |
| 2004/0074491 A1 | 4/2004 | Hendricksen et al. | |
| 2004/0089306 A1 | 5/2004 | Hundertmark et al. | |
| 2004/0134487 A1 | 7/2004 | Deem et al. | |
| 2004/0148035 A1 | 7/2004 | Barrett et al. | |
| 2004/0154621 A1 | 8/2004 | Deem et al. | |
| 2004/0211434 A1 | 10/2004 | Loomas et al. | |
| 2005/0016530 A1 | 1/2005 | McCutcheon et al. | |
| 2005/0051163 A1 | 3/2005 | Deem et al. | |
| 2005/0066974 A1 | 3/2005 | Fields et al. | |
| 2005/0087137 A1 | 4/2005 | Park et al. | |
| 2005/0145253 A1 | 7/2005 | Wilson et al. | |
| 2005/0161048 A1 | 7/2005 | Rapacki et al. | |
| 2005/0166925 A1 | 8/2005 | Wilson et al. | |
| 2005/0178389 A1 | 8/2005 | Shaw et al. | |
| 2005/0196344 A1 | 9/2005 | McCutcheon et al. | |
| 2006/0020347 A1 | 1/2006 | Barrett et al. | |

FOREIGN PATENT DOCUMENTS

| | | | |
|---|---|---|---|
| EP | 1078601 A2 | 2/2001 | |
| EP | 1151729 A1 | 11/2001 | |
| EP | 1078601 A3 | 5/2002 | |
| GB | 2324729 A | 11/1998 | |
| RU | 2140211 C1 | 10/1999 | |
| SU | 852321 A1 | 8/1981 | |
| SU | 1371700 A1 | 2/1988 | |
| SU | 1593651 A1 | 9/1990 | |
| WO | WO 94/26175 A1 | 11/1994 | |
| WO | WO 95/32018 A1 | 11/1995 | |
| WO | WO 96/34582 A1 | 11/1996 | |
| WO | WO 96/39960 A1 | 12/1996 | |
| WO | WO 97/44085 A2 | 11/1997 | |
| WO | WO 98/00840 A1 | 1/1998 | |
| WO | WO 98/19633 A1 | 5/1998 | |
| WO | WO 97/44085 A3 | 9/1998 | |
| WO | WO 98/39047 A1 | 9/1998 | |
| WO | WO 98/44854 A1 | 10/1998 | |
| WO | WO 98/48706 A1 | 11/1998 | |
| WO | WO 99/01076 A1 | 1/1999 | |
| WO | WO 99/13801 A1 | 3/1999 | |
| WO | WO 99/26692 A1 | 6/1999 | |
| WO | WO 99/32040 A1 | 7/1999 | |
| WO | WO 99/42059 A2 | 8/1999 | |
| WO | WO 99/42161 A2 | 8/1999 | |
| WO | WO 99/42161 A3 | 10/1999 | |
| WO | WO 99/42059 A3 | 11/1999 | |
| WO | WO 99/64109 A1 | 12/1999 | |
| WO | WO 00/15149 A1 | 3/2000 | |
| WO | WO 00/42950 A2 | 7/2000 | |
| WO | WO 00/51510 A1 | 9/2000 | |
| WO | WO 00/62699 A2 | 10/2000 | |
| WO | WO 00/42950 A3 | 11/2000 | |
| WO | WO 00/78386 A1 | 12/2000 | |
| WO | WO 00/78407 A1 | 12/2000 | |
| WO | WO 01/02042 A1 | 1/2001 | |
| WO | WO 01/03642 A1 | 1/2001 | |
| WO | WO 01/05334 A1 | 1/2001 | |
| WO | WO 01/10313 A1 | 2/2001 | |
| WO | WO 01/10314 A2 | 2/2001 | |
| WO | WO 01/12104 A1 | 2/2001 | |
| WO | WO 01/13839 A1 | 3/2001 | |
| WO | WO 01/13908 A2 | 3/2001 | |
| WO | WO 00/62699 A3 | 4/2001 | |
| WO | WO 01/28433 A1 | 4/2001 | |
| WO | WO 01/45590 A2 | 6/2001 | |
| WO | WO 01/49213 A2 | 7/2001 | |
| WO | WO 01/54585 A1 | 8/2001 | |
| WO | WO 01/54625 A1 | 8/2001 | |
| WO | WO 01/54685 A1 | 8/2001 | |
| WO | WO 01/66190 A2 | 9/2001 | |
| WO | WO 01/74271 A1 | 10/2001 | |
| WO | WO 01/87170 A1 | 11/2001 | |
| WO | WO 01/89366 A2 | 11/2001 | |
| WO | WO 01/95786 A2 | 12/2001 | |
| WO | WO 01/13908 A3 | 1/2002 | |
| WO | WO 01/49213 A3 | 1/2002 | |
| WO | WO 02/05884 A2 | 1/2002 | |
| WO | WO 01/45590 A3 | 3/2002 | |
| WO | WO 02/22072 A2 | 3/2002 | |
| WO | WO 01/95786 A3 | 4/2002 | |
| WO | WO 02/32333 A1 | 4/2002 | |
| WO | WO 02/34322 A2 | 5/2002 | |
| WO | WO 02/38038 A2 | 5/2002 | |
| WO | WO 02/47575 A2 | 6/2002 | |
| WO | WO 02/056794 A2 | 7/2002 | |
| WO | WO 02/064045 A1 | 8/2002 | |
| WO | WO 02/064190 A2 | 8/2002 | |
| WO | WO 02/069823 A2 | 9/2002 | |
| WO | WO 02/064190 A3 | 10/2002 | |
| WO | WO 02/056794 A3 | 11/2002 | |
| WO | WO 02/069823 A3 | 11/2002 | |
| WO | WO 02/094087 A1 | 11/2002 | |
| WO | WO 02/47575 A3 | 12/2002 | |
| WO | WO 02/34322 A3 | 1/2003 | |
| WO | WO 03/022124 A2 | 3/2003 | |
| WO | WO 03/030975 A2 | 4/2003 | |
| WO | WO 02/38038 A3 | 5/2003 | |
| WO | WO 03/041779 A1 | 5/2003 | |
| WO | WO 01/66190 A3 | 8/2003 | |
| WO | WO 02/022072 A3 | 8/2003 | |
| WO | WO 03/022124 A3 | 8/2003 | |
| WO | WO 03/030975 A3 | 8/2003 | |
| WO | WO 03/075796 A2 | 9/2003 | |
| WO | WO 03/099164 A1 | 12/2003 | |
| WO | WO 2004/010845 A2 | 2/2004 | |
| WO | WO 2004/010845 A3 | 6/2004 | |
| WO | WO 2004/049974 A2 | 6/2004 | |
| WO | WO 2004/049974 A3 | 8/2004 | |
| WO | WO 2005/007023 A2 | 1/2005 | |
| WO | WO 2005/007023 A3 | 5/2005 | |
| WO | WO 01/89366 A3 | 6/2009 | |

OTHER PUBLICATIONS

Article: "Autocath® 100—Nonsurgical, Intraurethral Bladder Control Device for Incontinent and Retentive Women—Dr. Kulisz's Development".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852-321, published Jul. 8, 1981, for: Treatment for acute pulmonary and pleural disease in children—by pneumo-abcessotomy simultaneous with occlusion of affected lung part.

Derwent# 007607249 WPI Acc. No. 1988-241181/198834 (citing Russian Application No. SU4026409, published Feb. 21, 1986.) Russian Patent No. SU 1371700.

Derwent# 008650867 WPI Acc. No. 1991-154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", J. Lab. ClinL Med., 9(iv):75-88, 1919.

Lewis et al., "Pulmonary Interstitial Emphysema: Selective Broncial Occlusion with a Swan-Ganz Catheter", Archives of Disease in Childhood, 63:313-315, 1988.

Mathew et al., "Selective bronchial obstruction for treatment of bullous interstitial emphysema." J. of Ped., 96:475-477, 1980.

Okada et al., "Emergent Bronchofiberoptic Bronchial Occlusion for Intractable Pneumothorax with Severe Emphysema", The Jap. J. of Thor. and Cardio. Sur., 46:1078-1081, 1998.

Puhakka et al., "Acute Bronchial Obstruction: An Experimental Rabbit Model Study", Int. J. of Pediatric Otorhinolaryngology, 18:107-118, 1989.

Snider et al., The Definition of Emphysema: Report of the National Heart Lung and Blood Institute, Division of Lung Diseases Workshop, Am. Rev. Respir. Dis., 132:182-185, 1985.

Woodring et al., "Pneumothorax ex Vacuo", Chest, 100:1102-1124, 1996.

European search report and opinion dated Aug. 10, 2011 for EP Application No. 11171223.8.

International search report and written report dated Aug. 5, 2005 for PCT/US2005/007881.

Office action dated Feb. 23, 2009 for U.S. Appl. No. 11/075,633.

Office action dated Mar. 26, 2010 for U.S. Appl. No. 11/075,633.

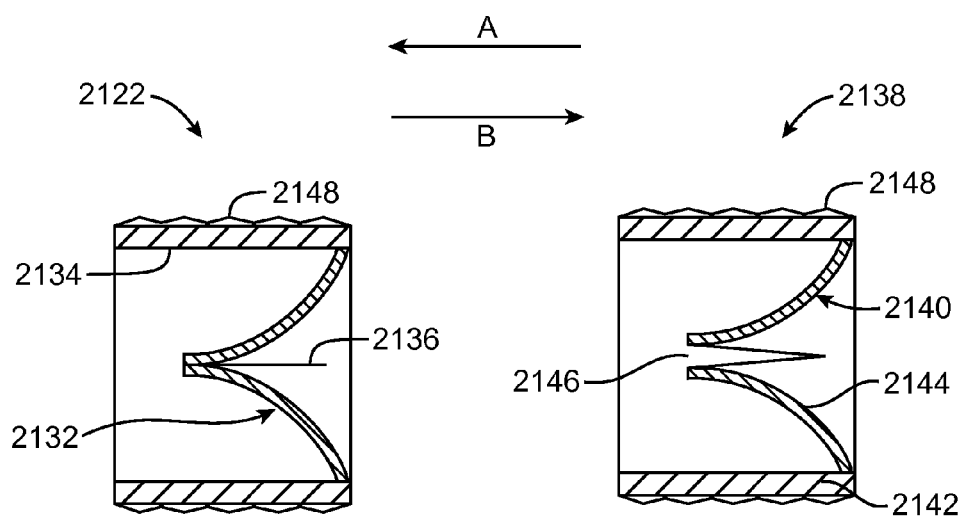

IMPLANTED BRONCHIAL ISOLATION DEVICES AND METHODS

CROSS-REFERENCES TO RELATED APPLICATIONS

This application is a continuation-in-part of co-pending application Ser. No. 11/075,633, filed on Mar. 8, 2005, which claimed priority from U.S. Provisional Patent Application Ser. No. 60/551,476 filed Mar. 8, 2004. This application is also a continuation-in-part of co-pending application Ser. No. 12/264,849, filed on Nov. 4, 2008, which was a continuation of application Ser. No. 11/395,396, filed on Mar. 30, 2006, now U.S. Pat. No. 7,662,181, which was a continuation of application Ser. No. 10/630,473, filed on Jul. 29, 2003, now U.S. Pat. No. 7,165,548, which was a continuation of application Ser. No. 09/519,735, filed on Mar. 4, 2000, now U.S. Pat. No. 6,679,264. The complete disclosure of each listed application are hereby incorporated by reference.

BACKGROUND OF THE INVENTION

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue.

Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, one or more flow control devices are implanted in airways feeding a diseased region of the lung to regulate fluid flow to the diseased lung region in order to fluidly isolate the region of the lung. These implanted flow control devices can be, for example, one-way valves that allow flow in the exhalation direction only, occluders or plugs that prevent flow in either direction, or two-way valves that control flow in both directions. However, such devices are still in the development stages.

Thus, there is much need for improvement in the design and functionality of such flow control devices.

BRIEF SUMMARY OF THE INVENTION

Disclosed are methods and devices for regulating fluid flow to and from a region of a patient's lung, such as to achieve a desired fluid flow dynamic to a lung region during respiration and/or to induce collapse in one or more lung regions. In one aspect, a flow control device suitable for implanting in a bronchial passageway is described. The flow control device comprises a valve defining a variable-sized mouth through which fluid can flow through the valve to regulate fluid flow through the bronchial passageway. The mouth increases in size in response to fluid flow in a first direction and decreases in size in response to fluid flow in a second direction. The mouth is open when the valve is in a default state.

In another aspect, there is described a fluid flow control device suitable for implanting in a bronchial passageway, comprising: a frame configured to retain the flow control device within the bronchial passageway; a seal coupled to the frame, the seal configured to seal against internal walls of the bronchial passageway; and a valve coupled to the frame, the valve having lips that define a variable-sized mouth through which fluid can flow through the valve, wherein the lips move away from one another to increase the size of the mouth in response to fluid flow in a first direction and move toward one another to decrease the size of the mouth in response to fluid flow in a second direction, and wherein the lips are at least partially spaced apart to define an open mouth when the valve is exposed to no fluid flow.

In another aspect, there is described a fluid flow control device suitable for implanting in a bronchial passageway, comprising a frame configured to retain the flow control device within the bronchial passageway; a seal coupled to the frame, the seal configured to seal against internal walls of the bronchial passageway; and a valve that resists fluid flow in an inspiratory direction through the bronchial passageway, wherein the valve's resistance to fluid flow varies as a function of a pressure differential across the valve.

In another aspect, there is described a fluid flow control device suitable for implanting in a bronchial passageway, comprising a frame configured to retain the flow control device within the bronchial passageway; a seal coupled to the frame, the seal configured to seal against internal walls of the bronchial passageway; and a valve that resists fluid flow in an inspiratory direction through the bronchial passageway, wherein the valve transitions to a state of increased resistance to fluid flow in response to an increase in a rate of fluid flow through the bronchial passageway.

In another aspect, there is described a flow control device suitable for implanting in a bronchial passageway, comprising a valve element that transitions between an open configuration that permits fluid flow in an inspiratory direction and a closed configuration that blocks fluid flow in the inspiratory direction, wherein a default state of the valve element is the open configuration.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 21 is an enlarged elevation view, in section, of a flow control element forming part of the system shown in FIG. 20, wherein the flow control element allows fluid flow in a first direction but blocks fluid flow in a second direction.

FIG. 22 is an enlarged elevation view, in section, of an alternative flow control element that allows fluid flow in a first direction but blocks fluid flow in a second direction.

DETAILED DESCRIPTION OF THE INVENTION

Disclosed are methods and devices for regulating fluid flow to and from a region of a patient's lung, such as to achieve a desired fluid flow dynamic to a lung region during respiration and/or to induce collapse in one or more lung regions. Pursuant to an exemplary procedure, an identified region of the lung (referred to herein as the "targeted lung region") is targeted for treatment. The targeted lung region is then bronchially isolated to regulate airflow into and/or out of the targeted lung region through one or more bronchial passageways that feed air to the targeted lung region.

Figure 1:
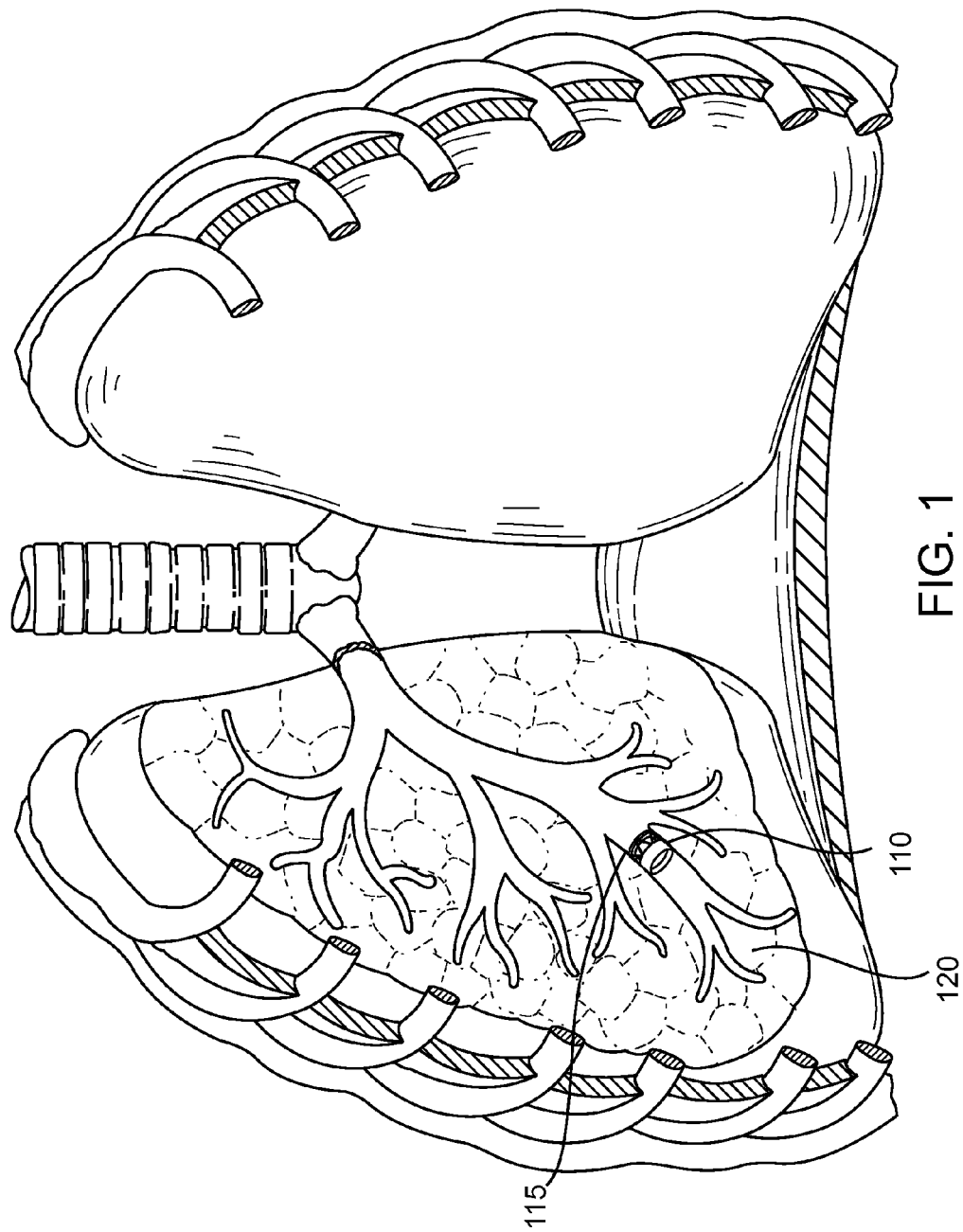
FIG. 1 shows an anterior view of a pair of human lungs and a bronchial tree with a flow control device implanted in a bronchial passageway to bronchially isolate a region of the lung.

As shown in FIG. 1, the bronchial isolation of the targeted lung region is accomplished by implanting a flow control device 110 (sometimes referred to as a bronchial isolation device) into a bronchial passageway 115 that feeds air to a targeted lung region 120. The flow control device 110 regulates fluid flow through the bronchial passageway 115 in which the flow control device 110 is implanted. The flow control device 110 can regulate airflow through the bronchial passageway 115 using a valve that permits fluid flow in a first direction (e.g., the exhalation direction) while limiting or preventing fluid flow in a second direction (e.g., the inhalation direction).

The valve includes coaptation regions, such as lips, that are moveable toward and away from one another so as to define a variable sized opening through which fluid can flow. When exposed to fluid flow in the first direction (e.g., the exhalation direction), the coaptation regions are urged away from one another to increase the size of the opening therebetween and permit an increasing amount of fluid flow through the valve. When exposed to fluid flow in the second direction (e.g., the inhalation direction), the coaptation regions are urged toward one another to decrease the size of and/or completely close the opening to decrease and/or completely prevent fluid flow through the valve. Flow through the valve is completely prevented when the coaptation regions are completely shut such that there is no opening for fluid to flow through the valve.

In conventional flow control devices, the valve is closed in a default state such that there is no gap or opening between the coaptation regions of the valve. The coaptation regions separate from one another to form an opening for fluid flow in the first direction when the valve cracking pressure is exceeded. For such a valve, there is a tendency for the coaptation regions, such as the valve lips, to stick together so as to resist opening and thereby increase the valve cracking pressure. The sticking force between the coaptation regions can be stronger when the valve is implanted in a lung, as mucous can coat the valve lips and form surface tension that must be overcome to separate the lips and open the valve.

As described in detail below, the flow control device 110 can include a valve that is "normally-open" in a default state such that at least a portion of the coaptation regions are separated from one another to define an opening therebetween. Because the coaptation regions are separated from one another in a default state, such a valve has a reduced cracking pressure as there is a little or no tendency for the coaptation regions to stick together. In addition, the gap between the coaptation regions reduces or eliminates the effect of surface tension caused by mucous on the valve. A normally-open valve also permits increased fluid flow in the first direction (relative to a valve that is closed in the default state), as the default open state of the valve reduces bulk resistance to flow in the first direction. Various embodiments and features of normally-open valves are described in more detail below.

Exemplary Lung Regions. Throughout this disclosure, reference is made to the term "lung region". As used herein, the term "lung region" refers to a defined division or portion of a lung. For purposes of example, lung regions are described herein with reference to human lungs, wherein some exemplary lung regions include lung lobes and lung segments.

Thus, the term "lung region" as used herein can refer, for example, to a lung lobe or a lung segment. Such nomenclature conform to nomenclature for portions of the lungs that are known to those skilled in the art. However, it should be appreciated that the term "lung region" does not necessarily refer to a lung lobe or a lung segment, but can refer to some other defined division or portion of a human or nonhuman lung.

Figure 2:
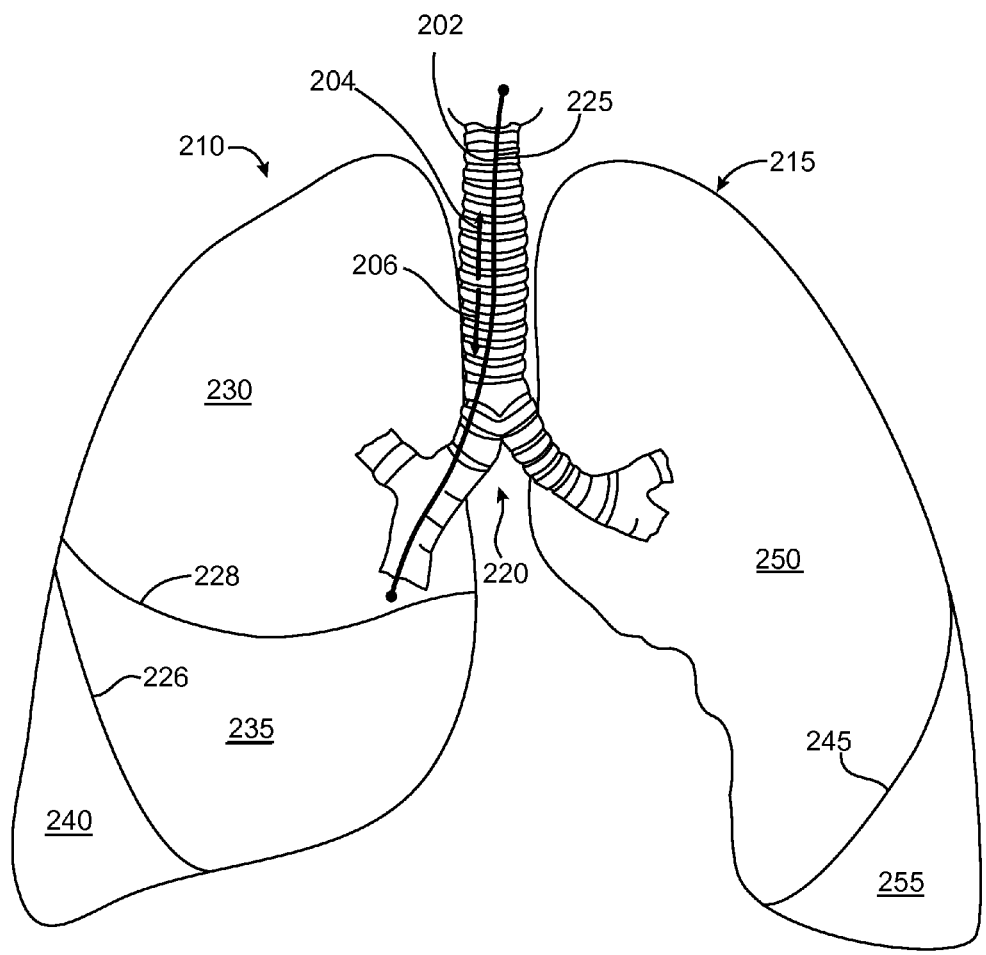
FIG. 2 illustrates an anterior view of a pair of human lungs and a bronchial tree.
Figure 5A:
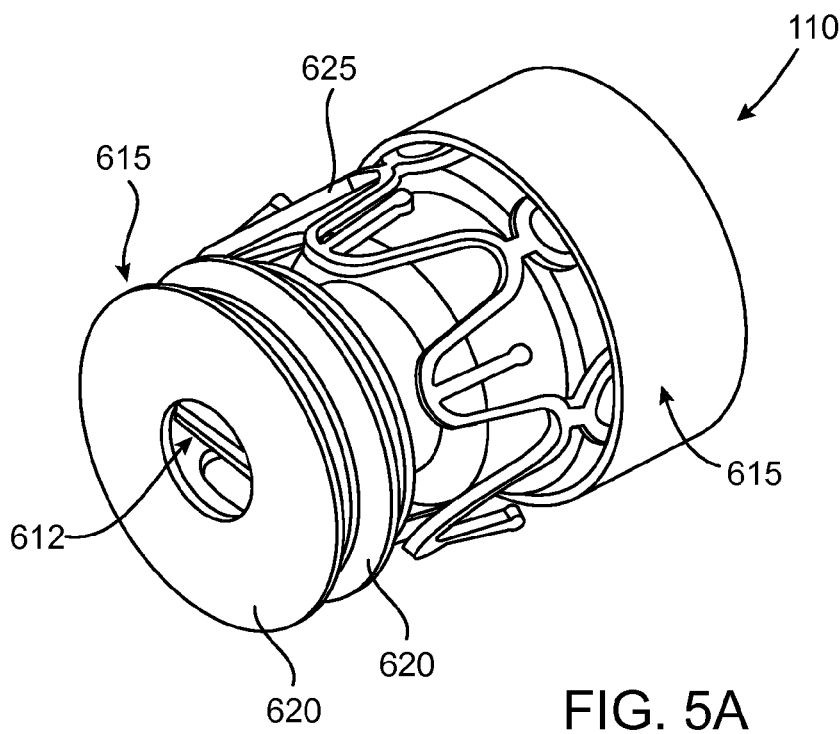
FIG. 5A shows a perspective view of an exemplary flow control device that can be implanted in a body passageway.

FIG. 2 shows an anterior view of a pair of human lungs 210,215 and a bronchial tree 220 that provides a fluid pathway into and out of the lungs 210,215 from a trachea 225, as will be known to those skilled in the art. As used herein, the term "fluid" can refer to a gas, a liquid, or a combination of gas(es) and liquid(s). For clarity of illustration, FIG. 2 shows only a portion of the bronchial tree 220, which is described in more detail below with reference to FIG. 5.

Throughout this description, certain terms are used that refer to relative directions or locations along a path defined from an entryway into the patient's body (e.g., the mouth or nose) to the patient's lungs. The path of airflow into the lungs generally begins at the patient's mouth or nose, travels through the trachea into one or more bronchial passageways, and terminates at some point in the patient's lungs. For example, FIG. 2 shows a path 202 that travels through the trachea 225 and through a bronchial passageway into a location in the right lung 210. The term "proximal direction" refers to the direction along such a path 202 that points toward the patient's mouth or nose and away from the patient's lungs. In other words, the proximal direction is generally the same as the expiration direction when the patient breathes. The arrow 204 in FIG. 2 points in the proximal or expiratory direction. The term "distal direction" refers to the direction along such a path 202 that points toward the patient's lung and away from the mouth or nose. The distal direction is generally the same as the inhalation or inspiratory direction when the patient breathes. The arrow 206 in FIG. 2 points in the distal or inhalation direction.

The lungs include a right lung 210 and a left lung 215. The right lung 210 includes lung regions comprised of three lobes, including a right upper lobe 230, a right middle lobe 235, and a right lower lobe 240. The lobes 230, 235, 240 are separated by two interlobar fissures, including a right oblique fissure 226 and a right transverse fissure 228. The right oblique fissure 226 separates the right lower lobe 240 from the right upper lobe 230 and from the right middle lobe 235. The right transverse fissure 228 separates the right upper lobe 230 from the right middle lobe 235.

As shown in FIG. 2, the left lung 215 includes lung regions comprised of two lobes, including the left upper lobe 250 and the left lower lobe 255. An interlobar fissure comprised of a left oblique fissure 245 of the left lung 215 separates the left upper lobe 250 from the left lower lobe 255. The lobes 230, 235, 240, 250, 255 are directly supplied air via respective lobar bronchi, as described in detail below.

Figure 3A:
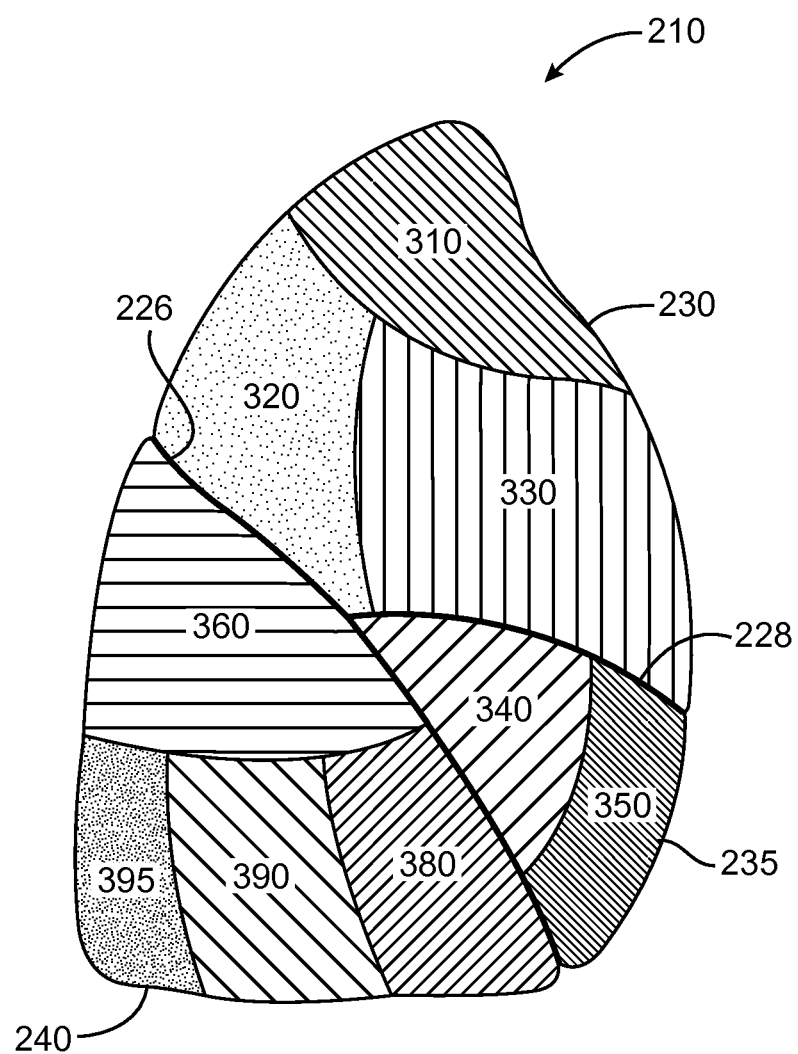
FIG. 3A illustrates a lateral view of the right lung.

FIG. 3A is a lateral view of the right lung 210. The right lung 210 is subdivided into lung regions comprised of a plurality of bronchopulmonary segments. Each bronchopulmonary segment is directly supplied air by a corresponding segmental tertiary bronchus, as described below. The bronchopulmonary segments of the right lung 210 include a right apical segment 310, a right posterior segment 320, and a right anterior segment 330, all of which are disposed in the right upper lobe 230. The right lung bronchopulmonary segments further include a right lateral segment 340 and a right medial segment 350, which are disposed in the right middle lobe 235. The right lower lobe 240 includes bronchopulmonary segments comprised of a right superior segment 360, a right medial basal segment (which cannot be seen from the lateral view and is not shown in FIG. 3A), a right anterior basal segment 380, a right lateral basal segment 390, and a right posterior basal segment 395.

Figure 3B:
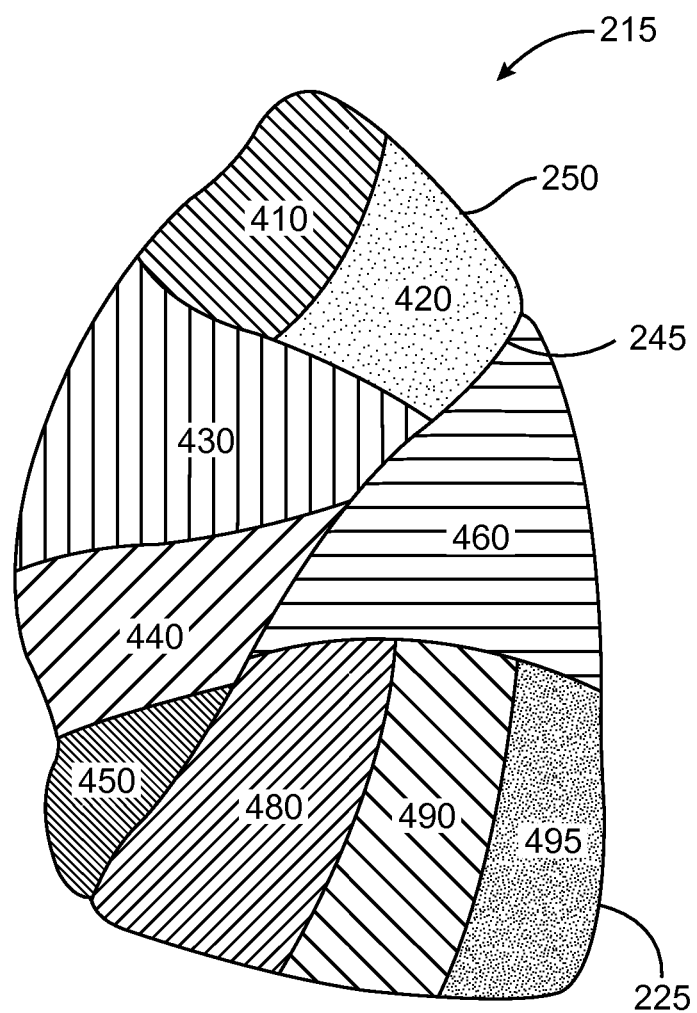
FIG. 3B illustrates a lateral view of the left lung.

FIG. 3B shows a lateral view of the left lung 215, which is subdivided into lung regions comprised of a plurality of bronchopulmonary segments. The bronchopulmonary segments include a left apical segment 410, a left posterior segment 420, a left anterior segment 430, a left superior segment 440, and a left inferior segment 450, which are disposed in the left lung upper lobe 250. The lower 15 lobe 225 of the left lung 215 includes bronchopulmonary segments comprised of a left superior segment 460, a left medial basal segment (which cannot be seen from the lateral view and is not shown in FIG. 3B), a left anterior basal segment 480, a left lateral basal segment 490, and a left posterior basal segment 495.

Figure 4:
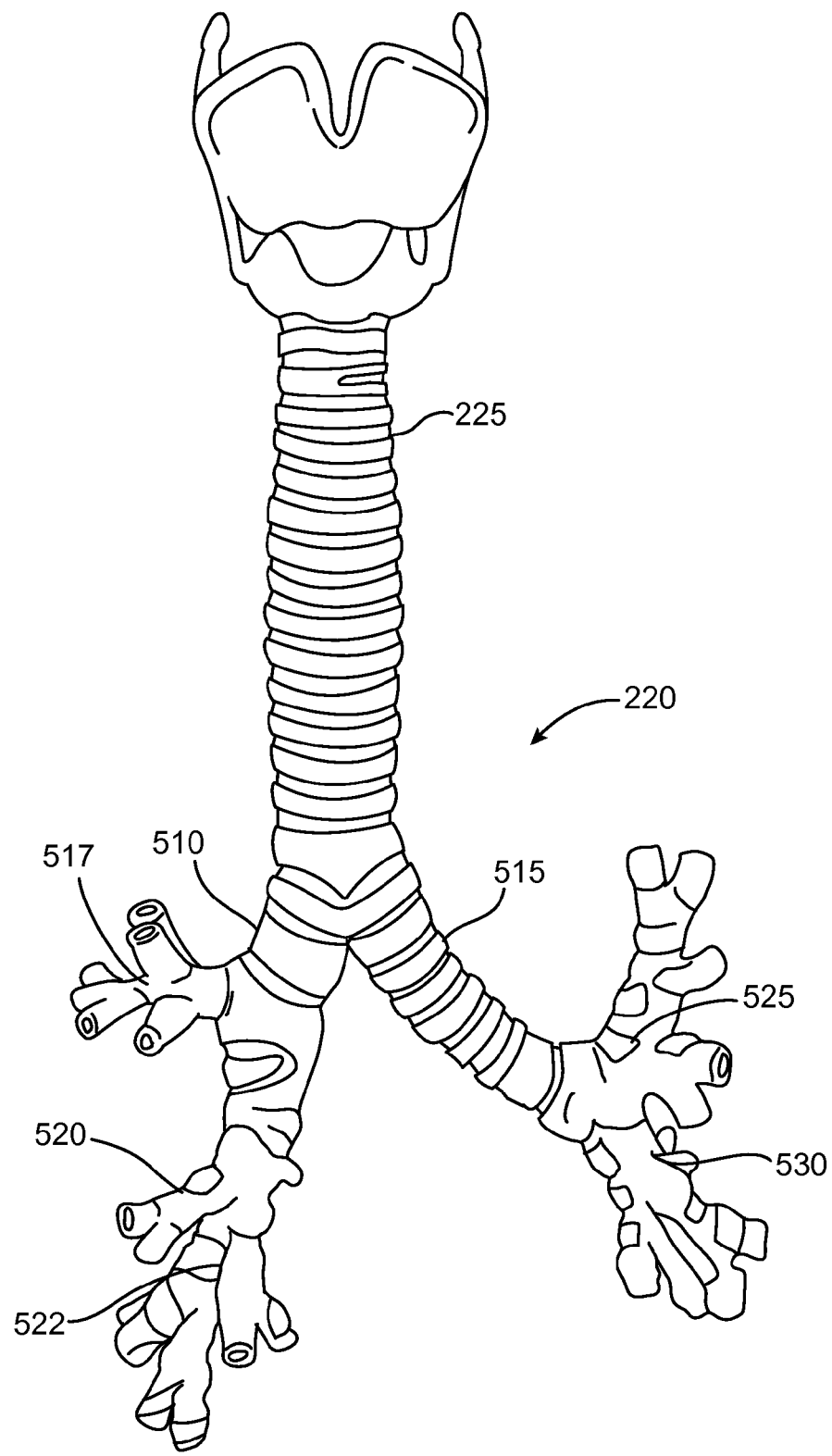
FIG. 4 illustrates an anterior view of the trachea and a portion of the bronchial tree.

FIG. 4 shows an anterior view of the trachea 225 and a portion of the bronchial tree 220, which includes a network of bronchial passageways, as described below. In the context of describing the lung, the terms "pathway" and "lumen" are used interchangeably herein. The trachea 225 divides at a lower end into two bronchial passageways comprised of primary bronchi, including a right primary bronchus 510 that provides direct air flow to the right lung 210, and a left primary bronchus 515 that provides direct air flow to the left lung 215. Each primary bronchus 510, 515 divides into a next generation of bronchial passageways comprised of a plurality of lobar bronchi. The right primary bronchus 510 divides into a right upper lobar bronchus 517, a right middle lobar bronchus 520, and a right lower lobar bronchus 522. The left primary bronchus 515 divides into a left upper lobar bronchus 525 and a left lower lobar bronchus 530. Each lobar bronchus, 517, 520, 522, 525, 530 directly feeds fluid to a respective lung lobe, as indicated by the respective names of the lobar bronchi. The lobar bronchi each divide into yet another generation of bronchial passageways comprised of segmental bronchi, which provide air flow to the bronchopulmonary segments discussed above.

As is known to those skilled in the art, a bronchial passageway defines an internal lumen through which fluid can flow to and from a lung or lung region. The diameter of the internal lumen for a specific bronchial passageway can vary based on the bronchial passageway's location in the bronchial tree (such as whether the bronchial passageway is a lobar bronchus or a segmental bronchus) and can also vary from patient to patient. However, the internal diameter of a bronchial passageway is generally in the range of 3 millimeters (mm) to 10 mm, although the internal diameter of a bronchial passageway can be outside of this range. For example, a bronchial passageway can have an internal diameter of well below 1 mm at locations deep within the lung.

Flow Control Device. Some of the breathing patterns that are characteristic of patients with severe emphysema are that the patients are able to inhale very easily and yet exhale with great difficulty. The destruction of lung parenchyma in the diseased regions of the lung leads to a loss of elastic recoil for the diseased lung region. The resulting imbalance in elastic recoil between diseased and healthier lung regions results in the diseased lung regions filling with air easily and first during inspiration. However, the diseased regions empty last and with great difficulty during expiration, as there is little or no elastic recoil remaining in the diseased lung regions to assist in the expelling of air. Adding to this difficulty, the distal airways in the diseased lung regions collapse during exhalation due to the loss of tethering forces that hold the airways open during exhalation in normal lung regions. As pleural pressure increases at the beginning of expiration, these distal airways partially or fully collapse, thus decreasing the exhalation flow, and increasing the work and time required for the patient to fully exhale.

To help ease the symptoms of emphysema and to improve breathing mechanics, implantation of one-way flow control devices or valve bronchial isolation devices has been employed, as described in several prior U.S. patent applications, including "Methods and Devices for use in Performing Pulmonary Procedures", Ser. No. 09/797,910, filed Mar. 2, 2001 and "Bronchial Flow Control Devices and Methods of Use", Ser. No. 10/270,792, filed Oct. 10, 2002, which are incorporated herein by reference. In the aforementioned patent applications, at least some of the bronchial isolation devices include one-way valves that remain closed and sealed in a default state, such as when there is no pressure differential across the valve.

FIGS. 5A-6B show an exemplary embodiment of a flow control device 110 that generally includes a valve, a frame or anchor, and a seal member for sealing against a wall of a bronchial passageway. It should be appreciated that the flow control device 110 shown in FIGS. 5A-6B is exemplary and that the frame, seal member, and valve can vary in structure. For example, the valve does not have to be configured with a central opening for fluid flow. Rather, the valve can be configured to interact with the walls of the bronchial passageway to permit or block fluid flow in that the valves contact or withdraw from the bronchial walls to block or permit fluid flow. The flow control device 110 has a general outer shape and contour that permits the flow control device 110 to fit entirely or at least partially within a body passageway, such as within a bronchial passageway.

The valve is configured to regulate fluid flow through a bronchial passageway in which the device 110 is implanted. The valve opens and vents fluid (such as gas or liquid, including mucous) when the pressure across the valve due to flow in a first direction, such as the exhalation direction, exceeds the rated cracking pressure of the valve. Thus, the valve opens in response to fluid flow in the first direction. The valve moves towards a closed configuration in response to fluid flow in a second, opposite direction such as the inhalation direction.

Figure 5B:
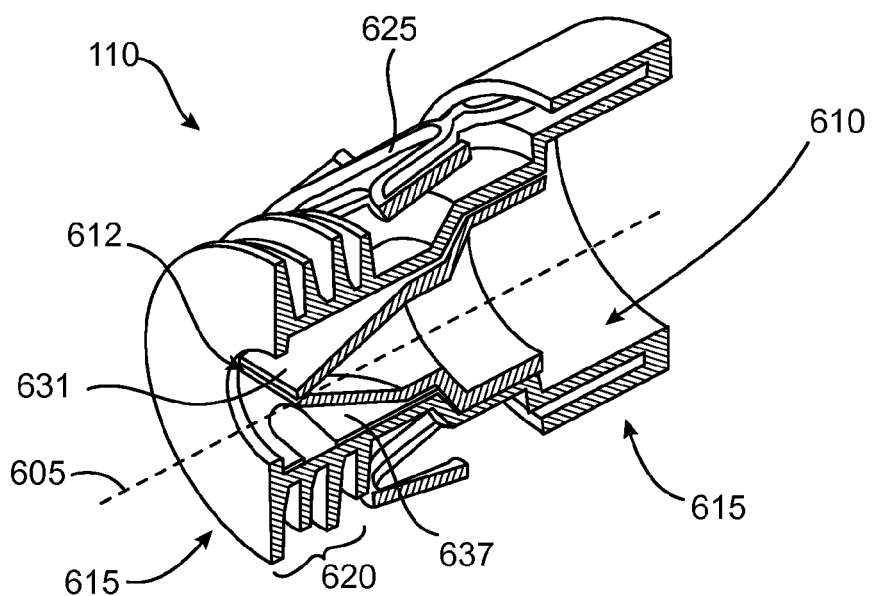
FIG. 5B shows a perspective, cross-sectional view of the flow control device of FIG. 5A.
Figure 6A:
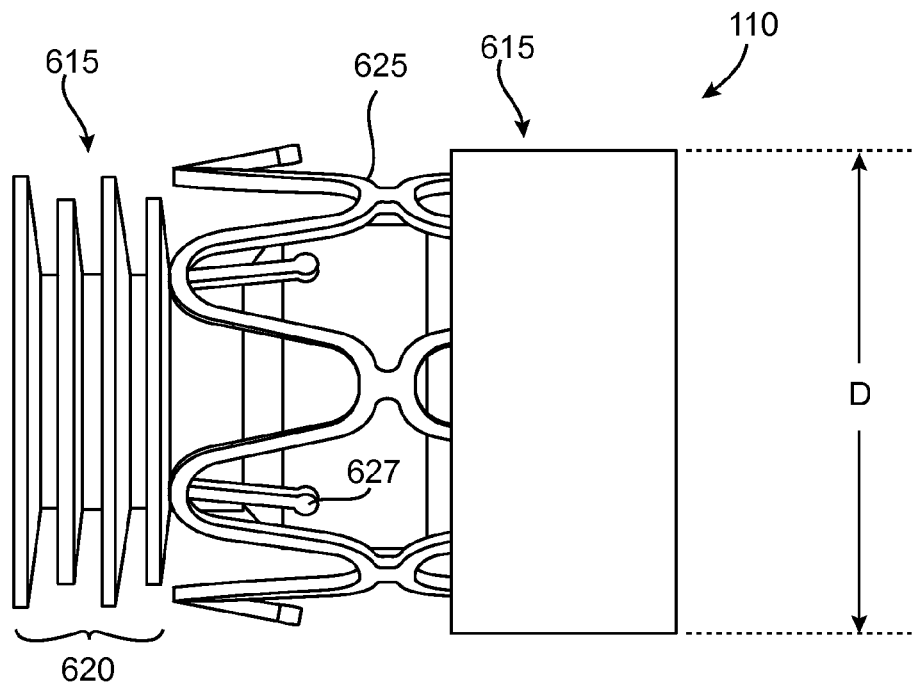
FIG. 6A shows a side view of the flow control device of FIG. 5A.
Figure 6B:
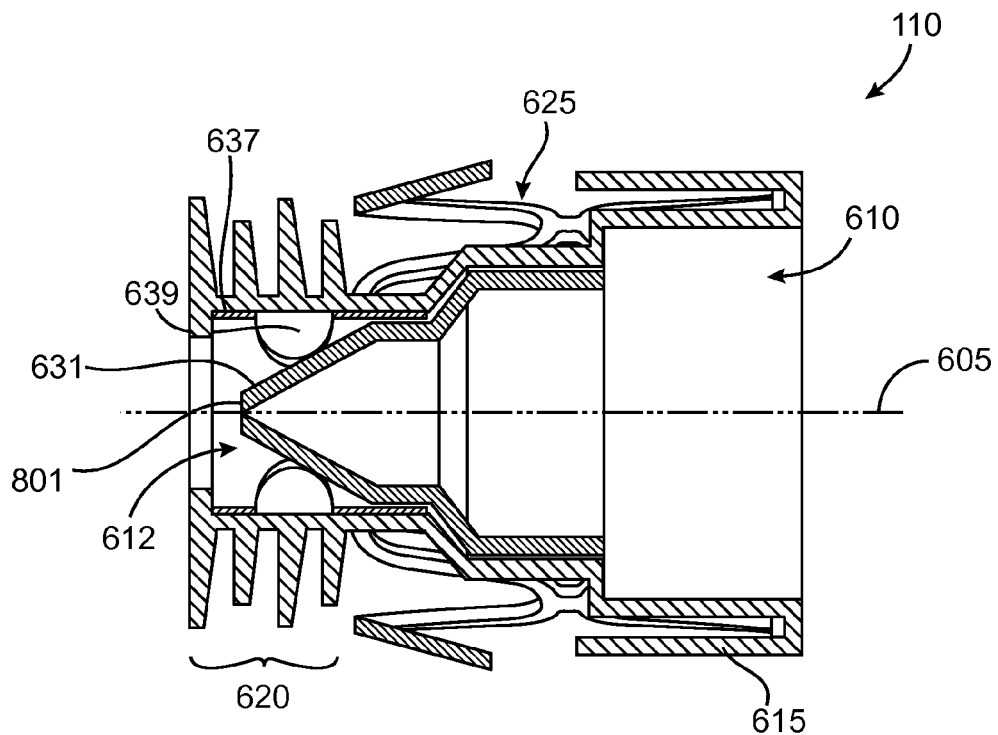
FIG. 6B shows a cross-sectional, side view of the flow control device of FIG. 5A.

With reference to FIGS. 5A-6B, the flow control device 110 extends generally along a central axis 605 (shown in FIGS. 5B and 6B). The flow control device 110 includes a main body that defines an interior lumen 610 through which fluid can flow along a flow path. The dimensions of the flow control device 110 can vary based upon the bronchial passageway in which the flow control device 110 is configured to be implanted. The valve does not have to be precisely sized for the bronchial passageway it is to be placed within. Generally, the diameter D (shown in FIG. 6A) of the flow control device 110 in the uncompressed state is larger than the inner diameter of the bronchial passageway in which the flow control device 110 will be placed. This will permit the flow control device 110 to be compressed prior to insertion in the bronchial passageway and then expand upon insertion in the bronchial passageway, which will provide for a secure fit between the flow control device 110 and the bronchial passageway.

The flow of fluid through the interior lumen 610 is controlled by a valve 612 that is disposed at a location along the interior lumen such that fluid must flow through the valve 612 in order to flow through the interior lumen 610. It should be appreciated that the valve 612 could be positioned at various locations along the interior lumen 610. The valve 612 can be made of a biocompatible material, such as a biocompatible polymer, such as silicone. As discussed in more detail below, the configuration of the valve 612 can vary based on a variety of factors, such as the desired cracking pressure of the valve 612.

The valve 612 can be configured to permit fluid to flow in only one-direction through the interior lumen 610, to permit regulated flow in two-directions through the interior lumen 610, or to prevent fluid flow in either direction.

With reference still to FIGS. 5A-6B, the flow control device 110 includes a seal member 615 that provides a seal with the internal walls of a body passageway when the flow control device is implanted into the body passageway. The seal member 615 is manufactured of a deformable material, such as silicone or a deformable elastomer. The flow control device 110 also includes an anchor member or frame 625 that functions to anchor the flow control device 110 within a body passageway.

As shown in FIGS. 5A-6B, the seal member 615 can includes a series of radially-extending, circular flanges 620 that surround the outer circumference of the flow control device 110. The configuration of the flanges can vary. For example, as shown in FIG. 6B, the radial length of each flange 620 can vary. It should be appreciated that the radial length could be equal for all of the flanges 620 or that the radial length of each flange could vary in some other manner. In addition, the flanges 620 can be oriented at a variety of angles relative to the longitudinal axis 605 of the flow control device.

As mentioned, the anchor member 625 functions to anchor the flow control device 110 in place when the flow control device is implanted within a body passageway, such as within a bronchial passageway. The anchor member 625 has a structure that can contract and expand in size (in a radial direction and/or in a longitudinal direction) so that the anchor member can expand to grip the interior walls of a body passageway in which the flow control device is positioned. In one embodiment, as shown in FIGS. 5A-6B, the anchor member 625 comprises an annular frame that surrounds the flow control device 110.

The frame 625 can be formed from a super-elastic material, such as Nickel Titanium (also known as Nitinol), such as by cutting the frame out of a tube of Nitinol or by forming the frame out of Nitinol wire. The super-elastic properties of Nitinol can result in the frame exerting a radial force against the interior walls of a bronchial passageway sufficient to anchor the flow control device 110 in place.

It should be appreciated that the configurations, including the sizes and shapes, of the frame 625 and the seal member 615 can vary from those shown in the figures. The seal 615 and/or the frame 625 can contract or expand in size, particularly in a radial direction. The default state is an expanded size, such that the flow control device 110 will have a maximum diameter (which is defined by either the seal 615 or the frame 625) when the flow control device 110 is in the default state. The flow control device 110 can be radially contracted in size during insertion into a bronchial passageway, so that once the flow control device 110 is inserted into the passageway, it expands within the passageway.

At least a portion of the valve 612 is optionally surrounded by a rigid or semirigid valve protector member 637 (shown in FIGS. 5B and 6B), which is a tubular member or annular wall that is contained inside the seal member 615. In another embodiment, the valve protector can comprise a coil of wire or a ring of wire that provides some level of structural support to the flow control device. The valve protector 637 can be concentrically located within the seal member 615. Alternately, the valve 612 can be completely molded within the seal member 615 such that the material of the seal member 615 completely surrounds the valve protector. The valve protector has sufficient rigidity to maintain the shape of the valve member against compression.

In one embodiment, the valve protector member 637 has two or more windows 639 comprising holes that extend through the valve protector member, as shown in FIG. 6B. The windows 639 can provide a location where a removal device, such as graspers or forceps, can be inserted in order to facilitate removal of the flow control device 110 from a bronchial passageway.

Figure 7:
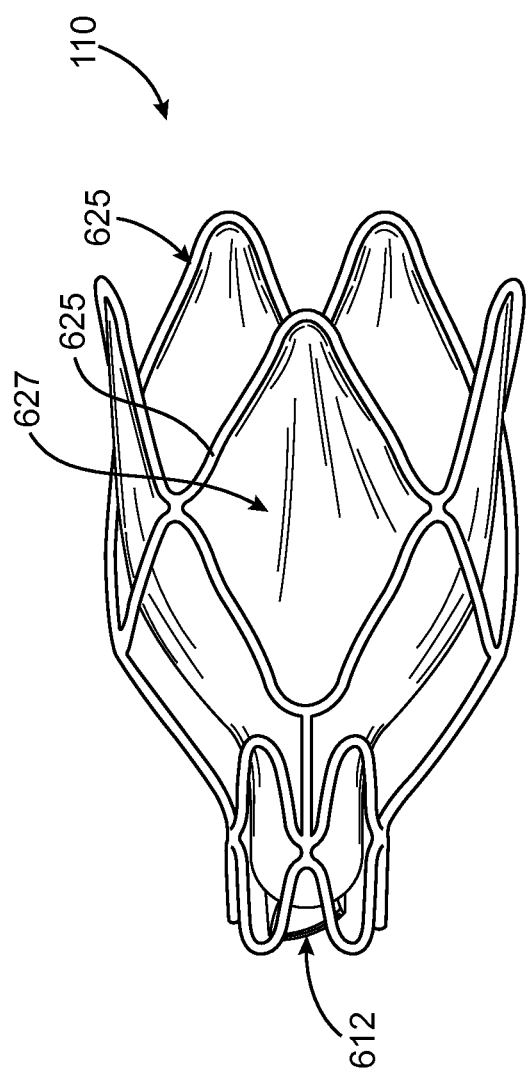
FIG. 7 shows another embodiment of a flow control device.

As mentioned, the structural configuration of the flow control device can vary. For example, FIG. 7 shows a perspective view of another embodiment of a flow control device 110 that includes a frame 625, a valve 612 mounted in the frame 625, and a membrane 627. The frame 625 and the membrane 627 can collectively or individually seal with an internal wall of a bronchial passageway.

Normally-Open Valves. As mentioned, the valve in a flow control device opens and vents fluid (such as gas or liquid, including mucous) when the pressure differential across the valve due to flow in the first direction, such as the exhalation direction, exceeds the rated cracking pressure of the valve. Applicant has determined that the lower the cracking pressure and the higher the level of fluid flow in the first direction through the valve once it has cracked, the better the performance of the flow control device for certain circumstances. This is because a greater amount of fluid (gas or liquid) will be expelled from the target lung region through the valve during exhalation.

In an effort to further improve the performance of the valve by lowering the cracking pressure and increasing the flow through the valve once cracked, the valve may be configured to be open in a default state. The valve is "open" in that there is an opening for fluid to flow through. The opening is typically defined by a gap between the coaptation regions of the valve, such as a gap between the lips of a valve. A valve that is open in the default state is referred to herein as a "normally-open" valve. In the default state, there is no pressure differential across the valve. Those skilled in the art will appreciate that a pressure differential can be achieved as a result of the valve being exposed to the flow of fluid. Thus, when a normally-open valve is in a default state, the coaptation regions of the valve are at least partially separated from one another to define a gap or opening therebetween.

As discussed above, exemplary implantable one-way valve flow control devices are shown in FIG. 5A-7. A valve of a flow control device includes regions (referred to herein as coaptation regions) that contact one another to block flow through the valve, and separate from one another to allow flow through the valve. The coaptation regions can contact one another along their entire length or area such that there is no gap between therebetween and the valve is completely closed. The coaptation regions can also partially contact one another such that there is at least a partial opening therebetween. For a normally-open valve, the coaptation regions at least form a partial opening in the default state.

The coaptation regions can comprise, for example, opposed lips that contact one another in a duckbill valve. For example, in the embodiment shown in FIGS. 5A-6B, the valve 612 comprises a duckbill valve that includes two opposed, inclined walls or flaps 631 (shown in FIGS. 5B and 6B) that are oriented at an angle with respect to one another. The flaps 631 can open and close with respect to one another so as to form an opening between coaptation regions comprised of lips 801 (FIG. 6B). The relative positions of the lips 801 determines the size of the opening in the valve 612. When the lips are in full contact with one another, there is no opening between the coaptation regions. The valve shown in FIGS. 5A-6B has such a configuration.

In conventional flow control devices, the valve coaptation regions are in full contact with one another in a default state, such as when there is no pressure differential across the valve. That is, the coaptation regions are in contact with one another such that there is no opening for fluid to flow through. As mentioned, the default state is the state of the valve when exposed to no fluid flow and, therefore, no pressure differential across the valve. When a valve is "closed" the valve coaptation regions contact one another so as to block flow through the valve when there is no pressure differential across the valve.

There are now described embodiments of valves that are normally-open in a default state. Thus, when there is no pressure differential across the valve, the coaptation regions (such as the lips of a duckbill valve) of the valve are not in contact with one another or only partially contact one another so as to form an opening therebetween. As discussed, such a valve has a reduced cracking pressure with respect to a valve that is closed in the default state. One reason for this is that the gap between the coaptation regions reduces or eliminates any "sticking force" between the coaptation region, which sticking force resists cracking of the valve. Another reason is that the gap between the lips reduces or eliminates surface tension that can be caused by mucous lining the coaptation regions. Such surface tension must be overcome in order to crack the valve. Furthermore, because the valve is at least partially open in the default state, bulk resilience of the valve is decreased so that the valve has less resistance to flow in the first direction than for a normally-closed valve at the same pressure. This can result in a higher flow through the valve in the first direction once the valve is cracked.

Figure 8:
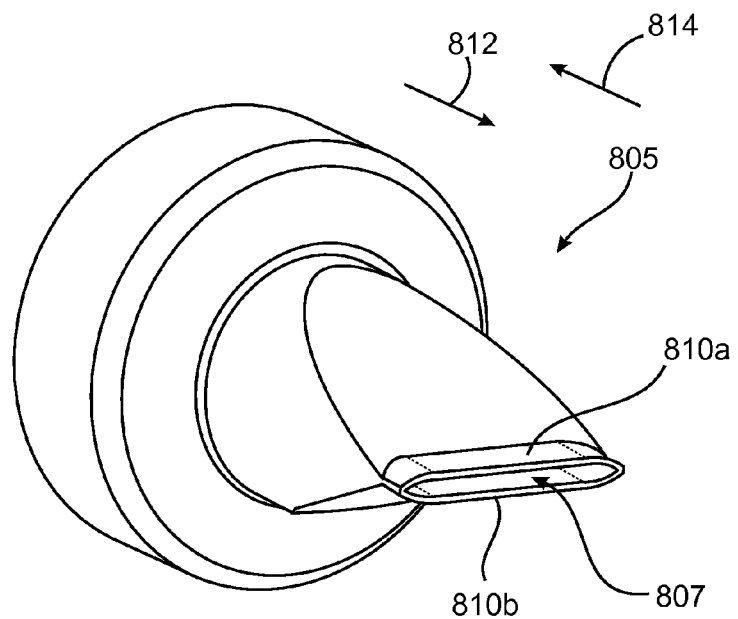
FIG. 8 shows a bi-leaflet valve with open mouth for use in a flow control device.

FIG. 8 shows an exemplary embodiment of a normally-open duckbill valve 805 that can be used in the flow control device 110. The valve 805 is manufactured with a measurable gap 807 between the coaptation regions. The coaptation regions comprise two or more lips 810a, 810b that are joined at opposing ends and that define the valve opening. The lips 810a, 810b do not contact one another along their length in a default state, but rather are separated to form the opening 807. When the valve 805 is exposed to flow in the first direction (e.g., the expiration direction, represented by arrow 812 in FIG. 8), the lips 810a and 810b are urged away from one another to increase the size of the opening 807. Because the lips 810a, 810b do not contact one another in the default, there is no sticking force to overcome in order for the flow in the first direction to urge the lips apart from each other. When the valve 805 is exposed to flow in the second direction (e.g., the inspiratory direction, represented by arrow 814 in FIG. 8) the lips 810a and 810b are urged toward one another. If exposed to a sufficient level of flow in the second direction, the lips 810a and 810b can fully contact one another to completely close the opening 807.

Figure 9:
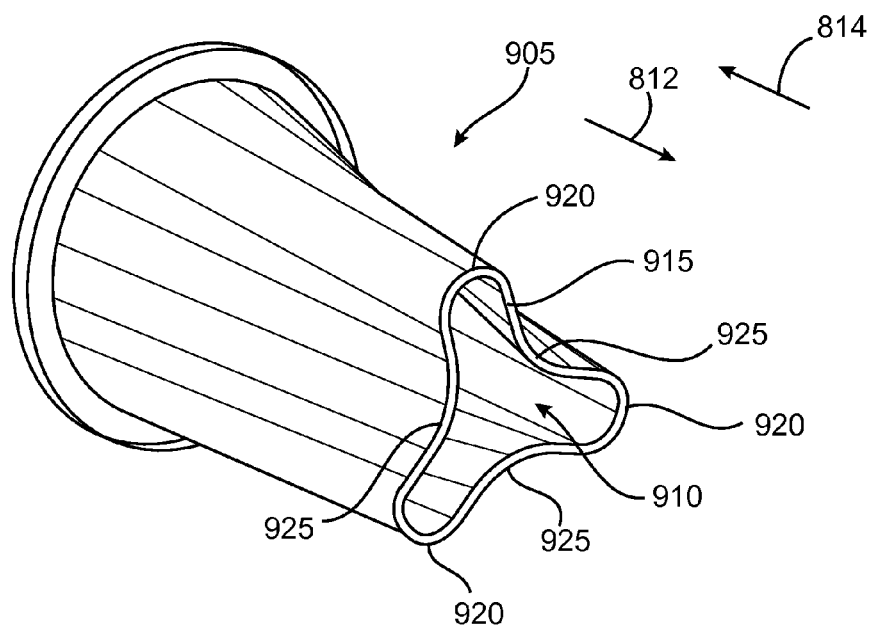
FIG. 9 shows a trilobular valve for use in a flow control device.

FIG. 9 shows another embodiment of a normally-open valve 905 having a trilobular configuration. The trilobular valve 905 has a single, contoured wall that is shaped so as to form three lobes defined by outside corners 920 and inside corners 925. The wall has coaptation regions comprised of lips 915 that define an opening 910 in a default state. When exposed to fluid flow in the first direction 812, the lips 915 separate to increase the size of the opening 910. When exposed to fluid flow in the second direction 814, the lips 915 move toward one another to decrease the size of the opening 910. The radius of the outside corners 920 and the inside corners 925 formed by the contours of the wall of the trilobular valve 905 can be gently curved as shown in FIG. 9, or can have a very sharp radius or can be sharp corners with no radius at all. Alternately, the valve may have four or more lobes.

Figure 10A:
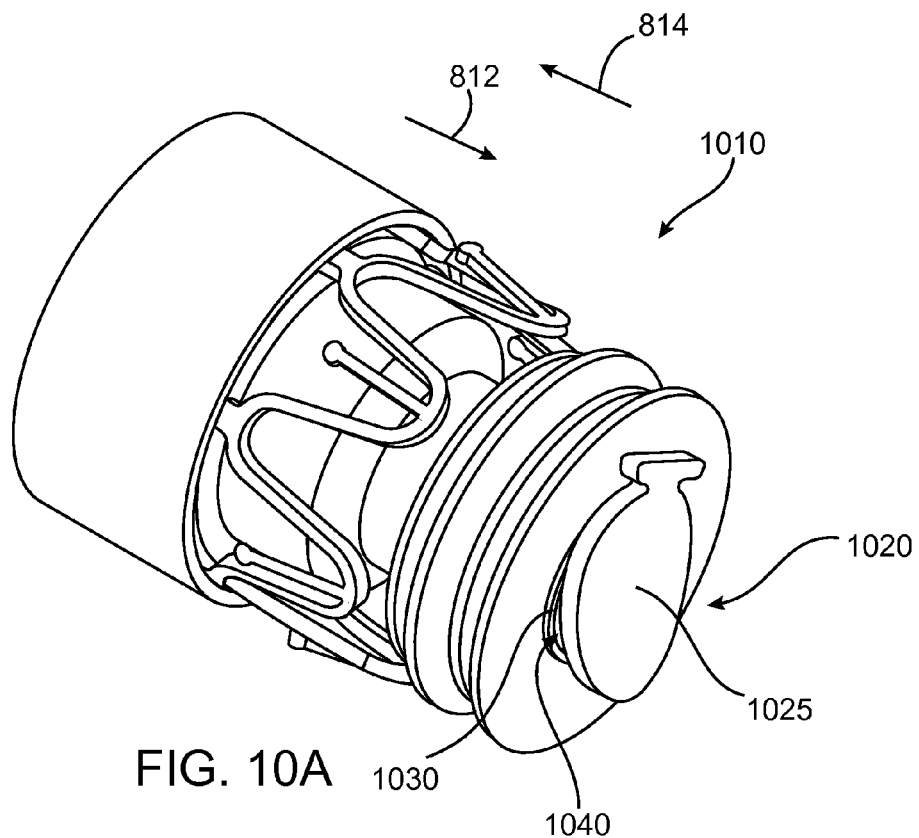
FIGS. 10A and 10B shows two views of a bronchial isolation device with an open-mouth flap valve.
Figure 10B:
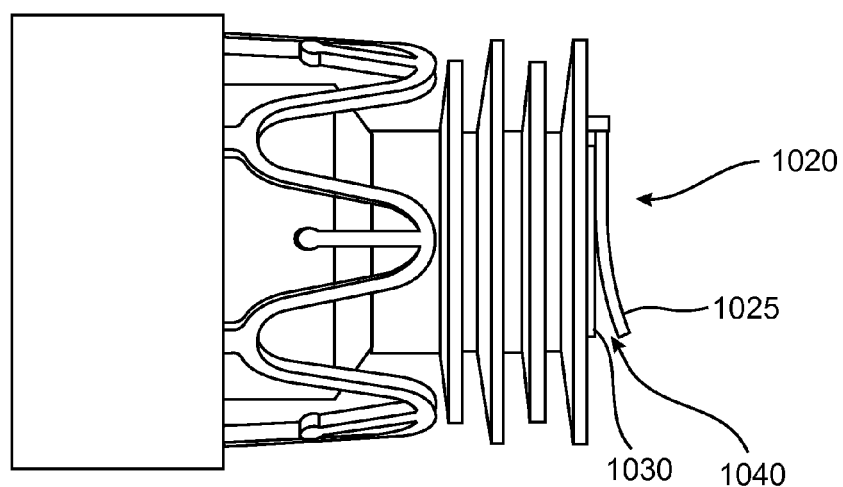

FIGS. 10A and 10B shows another embodiment of a flow control device 1010 that is similar in configuration to the device 110 described above. However, the flow control device 1010 has a valve 1020 having a flap valve configuration. The valve 1010 has a flap 1025 and a seat 1030. The flap 1025 opens and closes relative to the seat 1030. There is a measurable gap or opening 1040 between the flap 1025 and the seat 1030 in the default state of the valve 1010. The flap 1025 moves away from the seat 1030 in response to fluid flow in the first direction 812 to increase the size of the opening 1040 through which fluid flows. The flap 1025 moves toward the seat 1030 in response to fluid flow in the second direction 814 to decrease the size of the opening 1040. The flap 1025 can completely contact the seat 1030 to close the opening 1040 when exposed to a sufficient level of fluid flow in the second direction.

As discussed, the use of a valve that is "normally-open" has the effect of reducing or eliminating the cracking pressure. A flow control device equipped with a normally-open valve, when implanted into a bronchial passageway of a patient, opens wider more quickly in response to fluid flow in the expiratory direction and with a lower driving pressure with respect to a valve that is closed in its default state. This leads to greater exhalation of fluid during exhalation.

Figure 11:
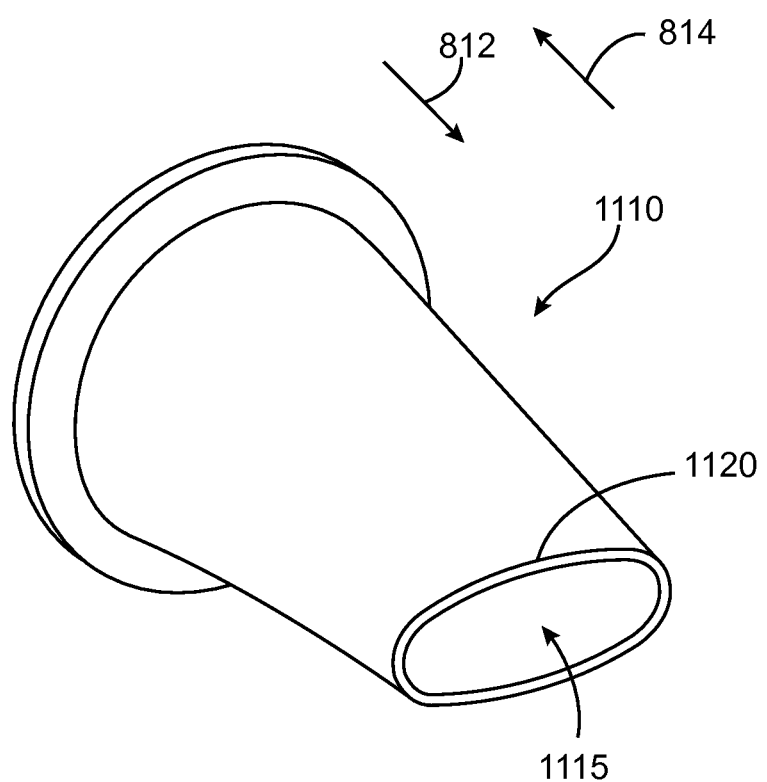
FIG. 11 shows an open, oval-mouth valve for use in a flow control device.

The size of the opening or amount of separation between the coaptation regions of the valve in the default state can vary. In one embodiment, the valve is completely open or near completely open in the default state. When a valve is "completely open" the valve allows its maximum, level of flow therethrough or a flow level that is substantially near its maximum. When a valve is "partially open", it allows less than the maximum level. FIG. 11 shows an exemplary valve 1110 that has an opening 1115 defined by lips 1120. The opening 1115 is oval-shaped in a default state. As in the previous valves, fluid flow in the first direction 812 urges the lips 1120 away from one another to increase the size of the opening 1115. Fluid flow in the second direction 814 urges the lips 1120 toward each other to decrease and possibly close the opening 1115.

In another embodiment, the valve is partially open in the default state and the valve opens more fully as the valve is exposed to fluid flow in a first direction, such as in the exhalation direction. The size of the opening decreases when exposed to fluid flow in the second direction, such as the inhalation direction. That is, the valve transitions from a partially open state toward a completely open state as the valve is exposed to an increasing level of fluid flow in the first direction. The valve might completely open when exposed to fluid flow in the first direction. How close the valve gets to being completely open depends on the level of flow in the first direction. When exposed to fluid flow in the second direction, the valve transitions from the partially open state toward the closed state. The valve might fully close depending on the level of flow in the second direction, although does not necessarily fully close. Thus, the opening in the valve increased as flow moves through the valve in the first direction, such as the exhalation direction. The valve shown in FIG. 8 shows an example of a valve that opens more fully when exposed to fluid flow in the first direction.

Given the variability in the degree, location and effect of the destruction due to emphysema and the resulting loss of elastic recoil and increase in distal airway collapse in patients that have emphysema, it can be difficult to assign a sufficiently low cracking pressure for the valve of a flow control device. The cracking pressure should be sufficiently low such that the valve will easily crack open and vent fluid during all conditions of flow in a particular direction, such as exhalation. In a similar fashion, it can be difficult to assign a required level of flow through the valve, once cracked, that will ensure that fluid will vent through the valve during exhalation. It is desirable to have the cracking pressure be as low as possible, and the level of flow through the valve, once cracked, to be as high as possible. If the valve is configured to open in response to exhalation flow, this results in the valve cracking open more quickly once exhalation has begun, and once open, the maximum possible flow of fluid will occur through the valve. This will result in the maximum emptying of fluid from the targeting lung unit during exhalation, and the maximum benefit to the patient.

When a valve is designed to be biased closed such that the valve is completely closed in a default state, the geometrical and material properties inherent in such a valve can add some degree of cracking pressure and some limitation to the level of flow through the valve. Applicant has determined that a valve has beneficial properties when the valve is not biased completely closed such that the coaptation regions do not contact one another when there is zero pressure differential across the valve. Such a valve opens with less resistance to flow and therefore allows much greater flow through it during exhalation (with respect to a valve that is closed in the default state). It should be appreciated that a normally-open valve can be biased toward the closed position but that the bias is not so strong as to completely close the valve. Thus, a normally-open valve can be biased toward a partially-closed configuration.

As mentioned, when the coaptation regions of a valve contact one another in the default state, the coaptation regions, typically formed of an elastomeric material, tend to stick together. The resulting "sticking force" must be overcome in order to crack the valve open, thus increasing the cracking pressure. This "sticking force" may be reduced by coating the coaptation regions with a material that reduces sticking between the coaptation regions. Some possible coatings include polytetrafluoroethylene (PTFE), perfluoroalkoxy (PFA), fluorinated ethylenepropylene (FEP) or other flouropolymer, parylene, hydrophilic coatings such as hyaluronic acid, various ion implanted or otherwise applied coatings such as silver, alumina ($Al_2O_3$) or sialon ($SiO_2$/N/$Al_2O_3$), etc. It should be appreciated that this is not a complete list of possible coatings or surface treatments, and other coatings or surface treatments that reduce the "sticking force" of the coaptation regions are possible. In addition, in order to ensure that the coaptation regions are always pressed together, a normally-closed valve is typically designed with some elastic resilience or spring bias so that some force from fluid flow through the valve must be applied to the coaptation regions in order to force them apart and allow fluid flow through the valve. This has the effect of raising the cracking pressure of the valve and of reducing the flow at a given driving pressure.

In designing a normally-open valve, there are a few design factors that can be considered. In general, if it is desired that the valve close at very low flows in the second direction (e.g., the inhalation direction), the valve will likely have some restriction to opening in response to fluid flow in the second direction (e.g., exhalation direction). If it is desired that the valve have the lowest possible restriction to exhaled flow, the valve will likely require a higher flow in the inhalation direction to close the valve. In addition, when closed, the valve may still allow a slight flow leak in the inhalation direction, which can be a disadvantage. Such a disadvantage may be more than compensated for by an increase in the flow through the valve in the exhalation direction. If the valve is of a duckbill or Heimlich type where there are two coaptation regions such as lips that come in contact with each other to seal the valve, the valve may be designed to have either of these characteristics or to be somewhere in between.

For example, if the valve is configured to be completely or almost completely open when there is no flow through the valve (such as for the valve 1110 shown in FIG. 11), the valve will have a very high flow rate in a first direction (e.g. the exhalation direction) yet will require a threshold amount of flow in the second direction (e.g., the inhalation direction) to close the valve.

The valve can also be configured to allow flow at a low rate to move through the valve without ever completely closing the valve at all. That is, the valve is completely or partially open when exposed to no fluid flow and gradually closes when exposed to flow in the second direction such that the valve increasingly closes as the rate of fluid flow in the second direction increases. When closed to a maximum closing capacity, the valve may have some leak paths that allow a low level of flow in the second direction, such as the inhalation direction. Such a valve 1210 is shown in FIG. 12 through FIG. 15. The valve 1210 is shown completely open in FIG. 12, which means that the valve is open to its maximum capacity. Alternately, the valve 1210 can be partially open in FIG. 12. In FIG. 13, the valve 1210 is partially closed in response to flow in the second direction (reverse flow). The lips of the valve are in partial contact with each other in FIG. 13. That is, the lips contact one another along a central region, but are separated from each other along opposed edges to form small openings at the opposed edges. It should be appreciated that the lips can contact each other at various locations along their length or area when in partial contact. In FIG. 14, the valve is completely closed by a higher level of flow in the second direction.

Thus, the valve provides increased resistance to fluid flow in the second direction as the level of fluid flow in the second direction increases. The valves described herein can be configured to provide increased resistance to fluid flow as the level or rate of fluid flow in the second direction increases. The fluid flow occurs as a result of a pressure differential across the valve. For example, the pressure differential may be such that fluid flows in the second direction (such as the inspiratory direction). In such a situation, the pressure on the proximal side of the valve is greater than the pressure on the distal side of the valve. As such a pressure differential increases, the valve's resistance to fluid flow in the inspiratory direction also increases. The resistance to fluid flow can gradually increase as the pressure differential and the rate of fluid flow increases. The valve's resistance to fluid flow can also suddenly increases when the pressure differential or rate of fluid flow increases beyond a threshold. The valve can resist fluid flow in an inspiratory direction through the bronchial passageway, wherein the valve transitions to a state of increased resistance to fluid flow in response to an increase in a rate of fluid flow through the bronchial passageway.

Depending on the design of the valve and the level of flow in the second direction, the valve may not necessarily reach the completely closed state shown in FIG. 14. Rather, the maximum closed state of the valve can be some variation of the valve as shown in FIG. 13, with the size(s) of the opening(s) between the lips being larger or smaller in the maximum closed state.

Figure 12:
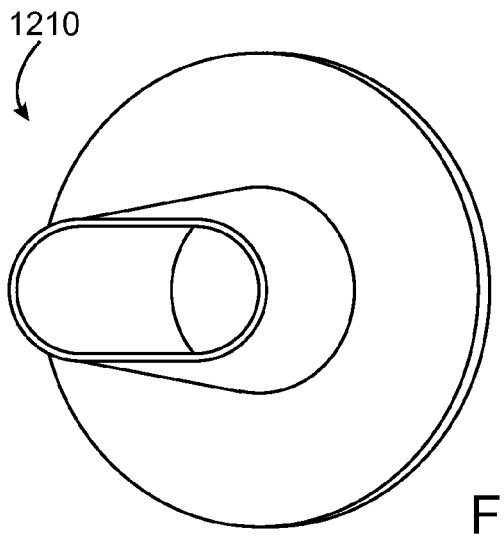
FIG. 12 shows a valve in a fully open state.
Figure 13:
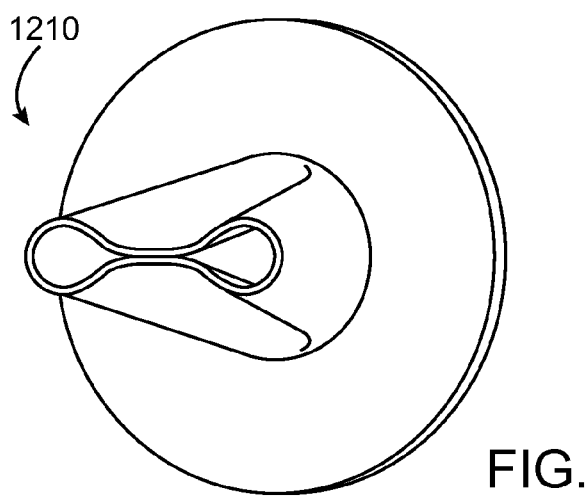
FIG. 13 shows a valve in a partially closed state.
Figure 14:
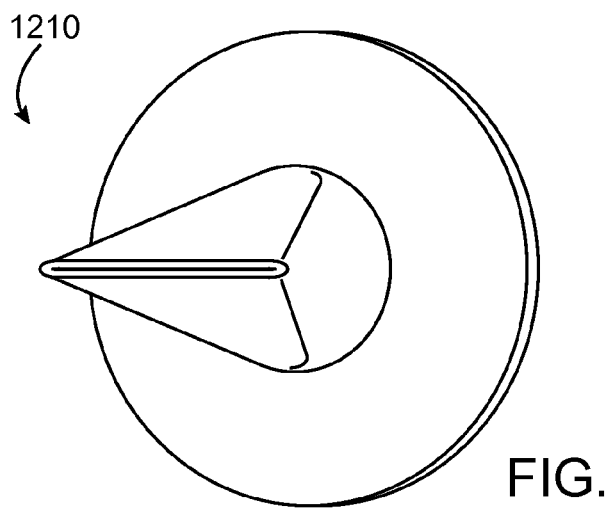
FIG. 14 shows a valve in a fully closed state.

As shown in FIGS. 12-14, depending on the level of flow through the valve in the second direction (e.g., the inhalation direction), there may be leak paths through the valve; such as in the corners of the valve mouth. The leak paths can allow some fluid flow through the valve when exposed to flow in the second direction, such as during inhalation. The valve gradually closes when exposed to increasing flow in the second direction and opens when exposed to flow in the first direction. It should be appreciated that the first direction need not correspond to the expiration direction and that the second direction need not correspond to the inhalation direction.

The valve of the flow control device can be configured so that it does not close suddenly, and may behave more like a variable resistance valve in that the resistance to flow in the second direction increases as the level of flow in the second direction through the valve increases, as shown in FIG. 12 through FIG. 14. Alternately, the valve may be configured to close quickly so that once a flow threshold required to close the valve is exceeded, the valve closes quickly. The valve in FIG. 8 is such a valve. If the valve is configured such that the coaptation regions are very close together when there is no flow through the valve (as shown in FIG. 8), the valve will have a lower flow in the first direction (e.g. exhalation direction) yet will close at a very low flow in the second direction (e.g. inhalation direction). When the valve is closed to a maximum, the valve may be designed to completely block flow in the second direction (such as under inhalation pressures and flows), or may allow a relatively low level of flow in the second direction. It should be appreciated that valves may be designed between these extremes and may be of other designs such as flap valves, trilobular valves, etc.

Figure 15:
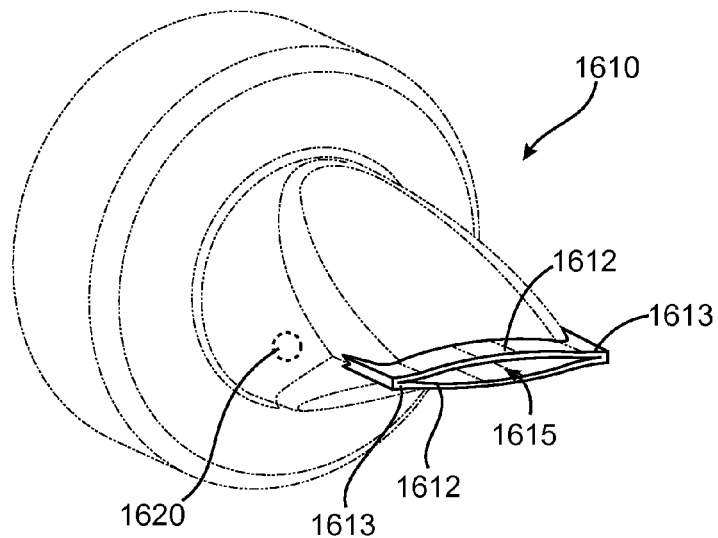
FIG. 15 shows a sharp-corner, open-mouth valve for us in a flow control device.
Figure 16A:
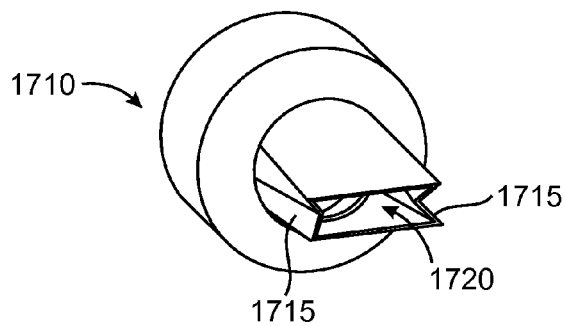
FIG. 16A-16C show various views of a high-flow valve with pleated sides.
Figure 16B:
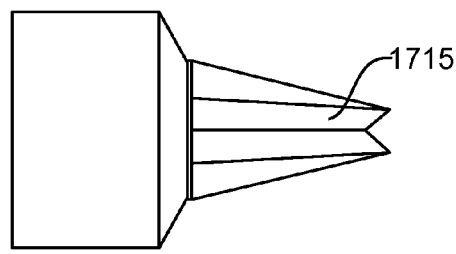
Figure 16C:
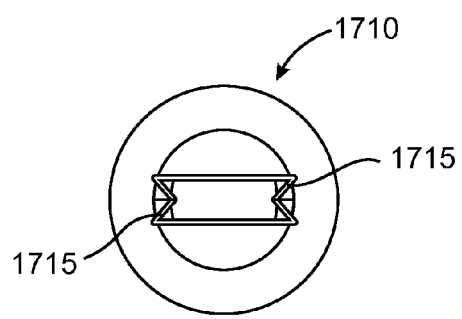

FIG. 15 shows another exemplary valve 1610. The valve 1610 has coaptation regions comprised of lips 1612 that meet at opposed corners 1613. The shape of the opening 1615 is defined by the lips 1612. In the illustrated embodiment, the corners 1613 of the opening 1615 form a very sharp angle, such as, for example, in the range of 1 to 10 degrees. It should be appreciated that the foregoing corner angles are exemplary and can vary. For example, the corner angle could be greater than 10 degrees. When such a valve closes, the two lips 1612 meet or contact one another tightly without leaving any openings therebetween. In this way, leaks in the second direction (e.g., the inhalation direction) may be prevented or reduced, while at the same time retaining the low cracking' pressure and high exhalation flow that come with a normally-open valve.

Another feature of the valve 1610 of FIG. 15 is the length (when measured along the central axis of the device in the fluid flow direction) of the valve lips 1612, which are longer than those found in the more standard duckbill valve shown mounted in the bronchial isolation device of FIG. 5A-7. In the valve 1610, the lips 1612 are parallel to one another for an extended length, such as, for example, approximately 0.010 to 0.100 inches. It should be appreciated that the extended lip length can vary based on the relative size of the valve. This extended length of the coaptation regions where the lips are parallel lowers the pressure required to close the valve in the inhalation direction while maintaining the low cracking pressure of a normally-open bi-leaflet valve.

In order to lower the crack pressure as much as possible and to increase the flow through the valve once it is cracked, the wall thickness of the valve walls for a duckbill valve may be reduced relative to conventional valve. If the valve is constructed of silicone, either molded or dipped, an optimal wall thickness may be as low as 0.002" or 0.003". As mentioned previously, the valve may also be constructed of other elastomeric materials, such as urethane.

When the valve is constructed with thin walls, the valve may be less resistant to inversion, or turning inside-out, when pressure is applied across the valve in the flow direction that closes the valve (such as in the inhalation direction). When a valve inverts, the valve ceases to perform as a one-way valve, so it is desirable to avoid inversion during expected inhalation flows and pressures. If a valve such as that shown in FIG. 15 is mounted into a flow control device, such as the device shown in FIG. 5A-7, the pressure at which inversion occurs may be greatly increased by bonding or otherwise attaching or "tethering" at least a portion 1620 of the valve, such as one side of the valve, to the inside of the valve protector member 637 (FIG. 5A) of the flow control device 110.

The attachment to the valve protector member 637 on one side of the valve greatly raises the pressure required for the valve to invert, yet does not greatly increase cracking pressure or reduce flow through the valve. Alternately, the valve may be bonded to the valve protector in two or more locations. In an alternative embodiment, the wall thickness of the valve component may be tapered so that it is thicker at the base of the valve to reduce inversion potential, yet is thinner at the mouth of the valve in order to keep the crack pressure low and the flow high.

Figure 19:
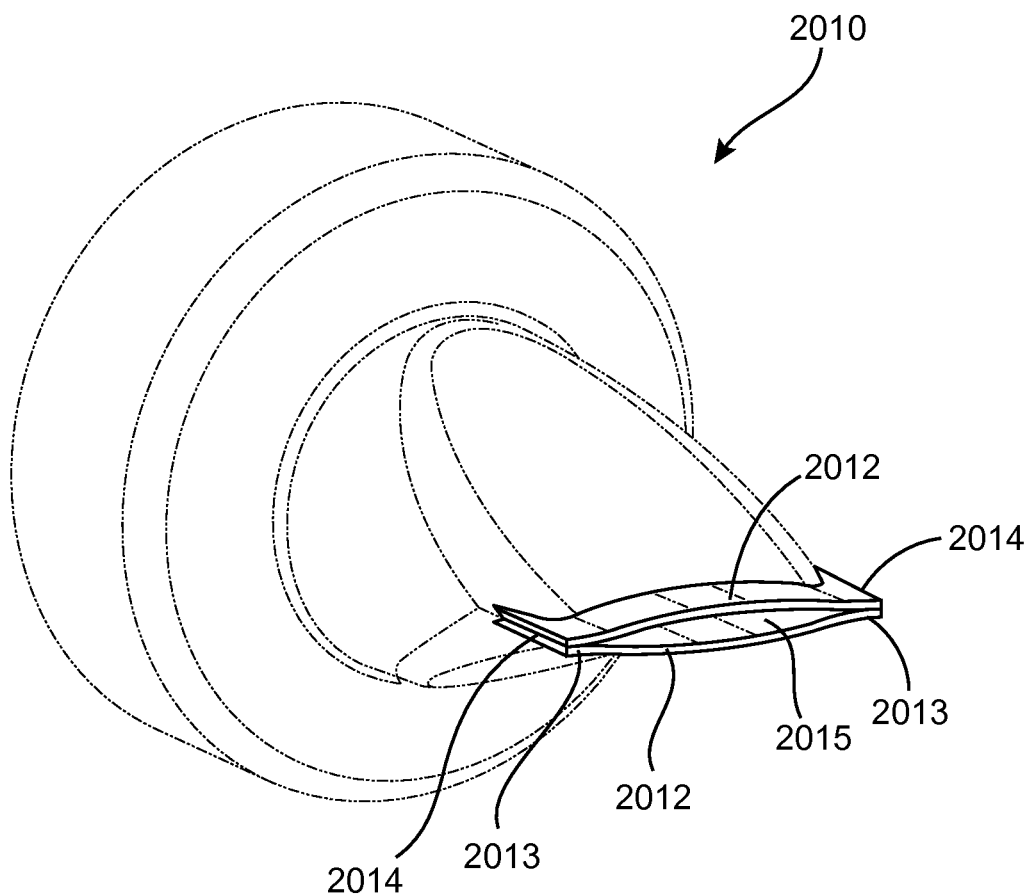
FIG. 19 shows another embodiment of a valve for use in a flow control device.

An alternate valve embodiment of a valve 2010 is shown in FIG. 19. In this embodiment, the valve 2010 has coaptation regions comprised of lips 2012 that meet at opposed corners 2013 in the same fashion as the valve shown in FIG. 15, however this embodiment differs in that the lips 2012 continue to be split apart around both sides of the valve 2014. This modification allows the valve to open farther and allows a larger level of flow in the exhalation direction. There is an opening 2015 in the default state that is defined by the lips 2012, however the valve may also be constructed without the opening 2015 in order to produce a valve which is not normally open in the default state.

An alternate valve embodiment of a valve 1710 is shown in FIGS. 17A-17C. In this embodiment, the valve 1710 has pleated sides 1715 and a mouth 1720 that is open in a default state. The pleated sides 1715 allow the valve 1710 to close and seal with minimal flow in the second direction (e.g. inhalation direction), yet when the flow is reversed and fluid starts to move through the valve in the first direction (e.g. exhalation direction), the pleats allow the valve to open very widely, thus allowing a very high flow rate.

Active Valve. The valves described above have been "passive" in that the valves open or close in response to flow and pressure across the valves. The valves can also close in response to a bias built into the valve. The aforementioned designs generally entail trade-offs between design and material properties. A normally-closed valve has the advantage of minimizing retrograde flow through the valve at the expense of increased cracking pressure and resistance to flow in the exhalation direction. A normally-open valve has the advantage of reducing cracking pressure and reducing resistance to flow in a first direction (e.g., the exhalation direction), but at the expense of increases in flow prior to valve closing in the second direction or leaking 20 after closure. Additionally, the physiological conditions at which valves must operate vary greatly between patients and even within the same patient under different conditions.

An "active" valve is actuated by some power source to open completely with little or no flow or pressure differential at the initiation of exhalation and then rapidly close and seal immediately at the initiation of inhalation. An active valve overcomes some drawbacks of passive valves. In a prior U.S. patent application entitled "Active Pump Bronchial Implant Devices and Methods of Use Thereof", Ser. No. 10/298,387, which is incorporated here by reference and assigned to the same assignee as the instant application, the inventors described various devices and methods of implantable pumps that would actively move fluid through the bronchial anatomy regardless of pressure and flow conditions across the valve. Under some 10 physiologic conditions or because of greater simplicity in design, the use of an active valve may be more desirable than a passive valve.

In one embodiment, the active valve is synchronized with the patient's breathing. One method is to convert the mechanical movement of the abdomen into an electrical pulse by having the patient wear an elastic belt with integrated pressure transducers about the abdomen. The pressure belt transmits this electrical signal, either wired, through radio waves or other methods, to a controller for the actuator of the implanted valve(s). Alternately sensing stimulation of the phrenic nerve during normal respiration can be used as the pacing signal to actuate the valve to open during exhalation and close during inhalation.

The active valve could be a flap valve, a bi-leaflet valve, a tri-leaflet valve, or any other valve that one skilled in the art could create.

Manufacture of Parallel-Lipped Valve. As discussed, a bi-leaflet or duckbill valve is configured with a relatively long coaptation region, such as lips that are parallel to each other as shown in FIGS. 15 and 19. This type of valve may be designed as a normally-open valve where the two parallel lips are spaced apart by a predetermined distance, or the valve may have the two lips that are in contact with each other along the length of the lips.

Figure 17:
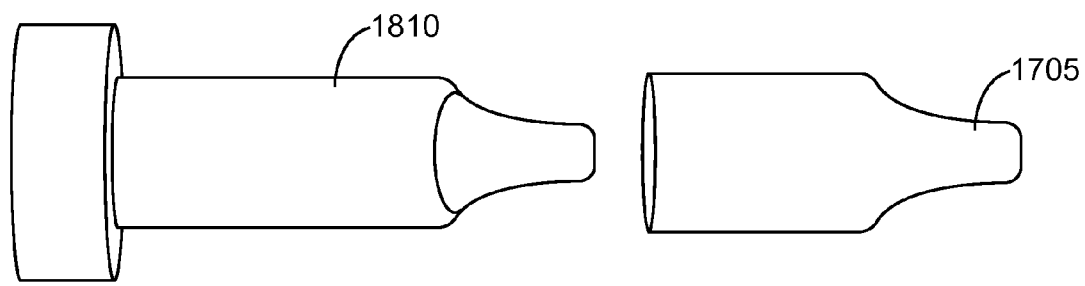
FIG. 17 shows a mandrel and a dipped" parallel-lipped valve manufactured using the mandrel for use in a flow control device.

In an embodiment shown in FIG. 17, a mandrel 1810 is formed out of aluminum, stainless steel or other suitable material in the shape of the desired inside surfaces of the valve. The mandrel 1810 is then dipped in a silicone, urethane or other suitable dispersion to coat the outer surface of the mandrel 1810. The coating is then cured in an appropriate fashion to form the valve, and the valve is stripped off of the mandrel 1810 as shown in FIG. 17. The tip 1705 of the valve is trimmed to expose the opening in the valve (as dipping will cover the tip of the mandrel thus closing off the opening at the valve mouth), thus leaving a valve with an open center lumen with parallel sealing surfaces. Of course, other methods of forming the normally-open, parallel-lipped valves such as injection molding, etc may be used.

Figure 18:
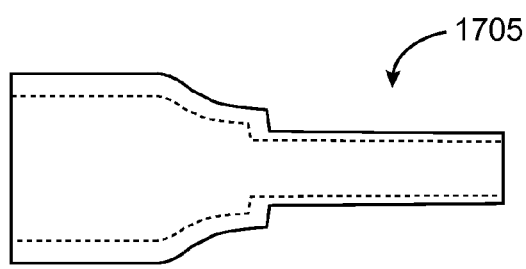
FIG. 18 shows a bonded parallel-lipped Heimlich valve.

Alternately, in the embodiment shown in FIG. 18, a parallel-lipped valve is normally-closed in that the lips are in contact with each other when there is no pressure differential across the valve. In this embodiment, the valve is formed by heat bonding two sheets of urethane to each other using a bonding die that is formed in the desired shape of the valve. Of course, other materials and methods could be used to form a normally-closed parallel lipped valve.

Tethered Flap Valve. For certain situations, it may be desirable to use a one-way flow control device that remains closed and sealed at all times when there is no flow through the device in either direction, yet still has as Iowa cracking pressure as possible in response to flow in the first direction, and once cracked, has as high a flow as possible through the valve. A flap valve is a style of valve that may be designed to have a low cracking pressure and a high flow once cracked. However, conventional flap valves do not remains closed and sealed with no flow through the valve. One way to improve the sealing of a flap valve is to add an elastic tether, formed for example from silicone, to the flap to assist in holding the valve down against the valve seat. For example, the flap valve 1010 shown in FIGS. 10A and 10B can have a tether mounted to the flap 1025 to urge the flap 1025 toward the seat 1030.

When a pressure differential is applied to the valve in the exhalation direction, the tether is stretched and the valve opens. When there is no pressure across the valve, the tether holds the flap against the valve seat, thus preventing leakage through the valve. In an alternative embodiment, the tether is not elastic and does not stretch when the valve opens. Instead, the edges of the flap component deflect away from the valve seat when the valve opens.

Occluder. There are times when an implanted occlusion flow control device, instead of a one-way or two-way valve device, is clinically indicated for the isolation of lung tissue. The device shown in FIG. 7 can be modified to act as an occluder. The valve 612 in FIG. 7 is replaced with an occluding member that blocks flow through the flow control device. As mentioned, the device 110 in FIG. 7 includes an elastically expandable frame 625 that is covered with an elastomeric membrane 627. In one embodiment, the device has an expanded frame laser-cut from nitinol tubing that has been expanded and heat treated to set it in the shape shown. The frame 625 is dipped in a silicone dispersion so that all outer surfaces are covered in a thin silicone membrane.

When the device is compressed into a delivery catheter, it may be delivered through the trachea, using any of a number of well know delivery methods, to the target bronchial lumen, and released from the catheter. Once released, the device expands and grip the walls of the bronchial lumen, and due to the silicone membrane, blocks fluid (gas and liquid) flow through the lumen in both the inhalation and exhalation directions. The frame 625 can have points or prongs on the distal end to prevent migration of the device in the distal or inhalation direction.

Of course, the frame may be made of other materials and take other shapes, may be deformable or heat expandable rather than spring resilient, and the membrane may be formed from other materials (such as urethane) and may be manufactured using methods other than dipping. This particular device is compact enough to fit into a delivery catheter that can fit through the working channel of a bronchoscope that has an internal diameter of 2.2 mm, however it may be delivered using other methods.

Figure 20:
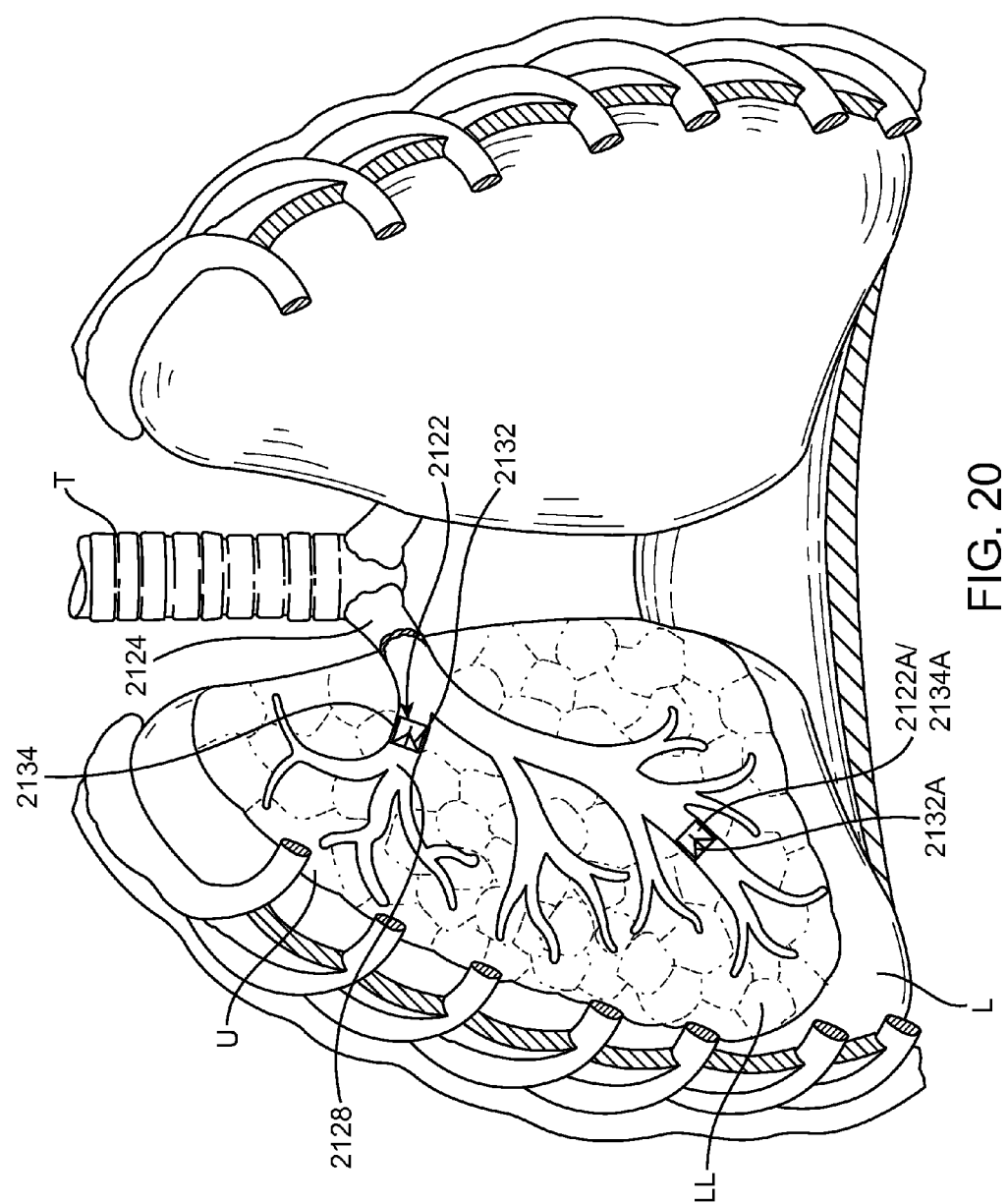
FIG. 20 is an enlarged elevation view of the lungs of a patient along with a further embodiment of the system of the invention.

FIG. 20 is an enlarged view of the patient's lungs L similar to that shown in FIG. 1. After the introducer and delivery device have been removed, the flow control element 2122 being left in the bronchiole 28. The flow control element 2122, shown in more detail in FIG. 21, is in the form of a valve with a valve member 2132 supported by a ring 2134. It should be noted that FIG. 20 also illustrates a second flow control element 2122A placed in a bronchiole 2128A that feeds a lower lobe LL of the lung. The flow control element 2122A includes a valve member 2132A and a support ring 2134A and reduces or prevents fluid from being inhaled into the hyper-expanded tissue of the lower lobe LL. It will be understood that any number of flow control elements may be used in a given procedure.

Referring to FIG. 21, which shows the flow control element 2122 in detail, the valve member 2132 is a duckbill-type valve and has two flaps defining an opening 2136. The valve member 2132 is shown in a flow-preventing orientation in FIG. 21 with the opening 2136 closed. The valve member 2132 is configured to allow fluid flow in a first direction (along arrow A) while controlling fluid flow in a second direction (along arrow B). In this embodiment, fluid flow in the direction of arrow B is controlled by being completely blocked by valve member 2132. The first and second directions in which fluid flow is allowed and controlled, respectively, are preferably opposite or substantially opposite each other, for example, as shown in the Figures. It will be appreciated, though, that the invention may be practiced with the first and second directions different but not opposite each other.

As noted above, the valve member 2132 of the flow control element 2122 controls fluid flow by completely blocking such flow in the second direction. As such, the valve member 2132 effectively functions as a one-way valve. Alternative embodiments of the invention utilize flow control elements that controls fluid flow in the second direction without completely blocking such flow.

FIG. 22 shows an exemplary flow control element 2138 constructed according to an alternative embodiment of the invention that limits, but does not block, fluid flow in at least one direction. The flow control element 2138 comprises a valve member 2140 supported by a ring 2142. The valve member 2140 is preferably a duckbill-type valve having a similar construction to that of the valve member 2132, except that the flaps 2144 are formed, secured, oriented or otherwise configured to maintain a flow opening 2146 when in their flow-controlling (as opposed to flow-allowing) orientation. The opening 2146 is sized and configured to achieve desired flow characteristics through the flow control element 2138.

When the flow control element 2138 is in its flow-allowing orientation (not shown), the flaps 2144 spread apart and allow essentially unimpeded fluid flow out of the diseased lung portion. When the flow control element 2138 is in its flow-controlling orientation, as shown in FIG. 22, the flaps move together to define opening 2146 which allows a predetermined amount of fluid to be inhaled into the lung portion. This is in contrast to flow control element 2122 which blocks fluid flow into the lung when in a flow-controlling orientation. It will of course be recognized that FIG. 22 shows only one way to achieve limited fluid flow in a given direction. The specific manner in which flow control is obtained may vary according to the invention, e.g., by varying the number, size, shape or position of the flow openings on the flow control element.

A number of embodiments of the invention have been described. Nevertheless, it will be understood that various modifications may be made without departing from 'the spirit and scope of the invention. Accordingly, other embodiments are within the scope of the following claims.

What is claimed is:

1. A flow control device suitable for implanting in a bronchial passageway, comprising:
a valve element comprising a first lip and a second lip, wherein the first and second lips are configured to transition the valve element between an open configuration that permits air flow in an expiratory direction and a closed configuration that blocks air flow in the inspiratory direction, wherein the first and second lips are configured to be substantially parallel to maintain an opening in a default state such that the first and second lips move away from one another to increase the size of the opening to a size larger than the size of the opening in the default state when exposed to air flow in the expiratory direction and the valve element transitions toward the closed configuration when exposed to air flow in the inspiratory direction;
wherein the valve element is in the default state when there is no pressure differential across the valve.

2. The flow control device of claim 1, wherein the valve is inclined to remain in the default state when not exposed to air flow through the bronchial passageway.

3. The flow control device of claim 1, wherein the valve progressively transitions toward the closed configuration as the level of air flow in the first direction increases.

4. A flow control device suitable for implanting in a bronchial passageway, comprising:
a valve defining a variable-sized mouth through which air can flow through the valve to regulate air flow when implanted in the bronchial passageway, wherein the mouth increases in size in response to air flow in a first direction and the mouth decreases in size in response to air flow in a second direction and wherein the valve includes coaptation regions comprising a first lip and a second lip that are connected at opposed corners that are parallel and define the mouth therebetween, the mouth being open when the coaptation regions are at least partially spaced apart from one another, wherein the first and second lips are at least partially spaced apart in a parallel fashion to keep the mouth open when exposed to no air flow, wherein the coaptation regions move away from one another to increase the size of the mouth to a size larger than the size of the mouth when exposed to no air flow in response to air flow in the first direction and move toward one another to decrease the size of the mouth in response to air flow in the second direction.

5. A flow control device as in claim 4, wherein the mouth can completely close to prevent air flow through the valve when the valve is exposed to a sufficient level of flow in the second direction.

6. The flow control device of claim 4, wherein the valve mouth progressively decreased in size as the level of air flow in the second direction increases.

7. The flow control device of claim 4, wherein the valve suddenly decreases in size when exposed to a level of air flow above a threshold level.

8. An air flow control device as in claim 4, wherein the valve comprises a duckbill valve and the coaptation regions comprise lips of the duckbill valve.

9. An air flow control device as in claim 4, wherein the coaptation regions are coated with a material that reduces sticking between the coaptation regions.

10. An air flow control device as in claim 4, wherein the mouth is oval when the valve is exposed to no air flow.

11. An air flow control device as in claim 4, wherein the lips defines a relative angle in the range of approximately 1 to 10 degrees at the corners.

12. An air flow control device suitable for implanting in a bronchial passageway, comprising:

a frame configured to retain the flow control device within the bronchial passageway;

a seal coupled to the frame, the seal configured to seal against internal walls of the bronchial passageway; and a valve coupled to the frame, the valve having lips that define a variable-sized mouth through which air can flow through the valve, wherein the lips are parallel and are at least partially spaced apart to define an open mouth when the valve is exposed to no air flow, and wherein the lips move away from one another to increase the size of the mouth to a size larger than the size of the mouth when the valve is exposed to no air flow in response to air flow in a first direction and the lips move toward one another to decrease the size of the mouth in response to air flow in a second direction.

13. An air flow control device as in claim 12, further comprising a valve protector that at least partially surrounds the valve, the valve protector having sufficient rigidity to maintain the shape of the valve member against compression, wherein at least a portion of the valve is bonded to the valve protector to prevent the valve from inverting.

* * * * *